United States Patent
Mullaney et al.

(10) Patent No.: US 9,532,805 B2
(45) Date of Patent: Jan. 3, 2017

(54) SINGLE LOCK EXTERNAL FIXATION CLAMP ARRANGEMENT AND METHOD

(71) Applicant: Zimmer, Inc., Warsaw, IN (US)

(72) Inventors: Michael W. Mullaney, Kinnelon, NJ (US); Stephen T. Miller, Scotts Valley, CA (US); William Brian Austin, Germantown, TN (US)

(73) Assignee: Zimmer, Inc., Warsaw, IN (US)

( * ) Notice: Subject to any disclaimer, the term of this patent is extended or adjusted under 35 U.S.C. 154(b) by 0 days.

(21) Appl. No.: 14/470,307

(22) Filed: Aug. 27, 2014

(65) Prior Publication Data
US 2014/0364853 A1    Dec. 11, 2014

Related U.S. Application Data

(63) Continuation of application No. 13/271,744, filed on Oct. 12, 2011, now Pat. No. 8,840,611.
(Continued)

(51) Int. Cl.
*A61B 17/00*    (2006.01)
*A61B 17/64*    (2006.01)

(52) U.S. Cl.
CPC .......... *A61B 17/6466* (2013.01); *A61B 17/645* (2013.01)

(58) Field of Classification Search
CPC ... A61B 17/60–17/666; A61B 17/70–17/7046; F16B 7/0493
See application file for complete search history.

(56) References Cited

U.S. PATENT DOCUMENTS

| 1,706,215 A | 3/1929 | Davidson |
| 2,705,603 A | 4/1955 | Bitz et al. |

(Continued)

FOREIGN PATENT DOCUMENTS

| DE | 2430234 A1 | 1/1975 |
| EP | 1820461 A1 | 8/2007 |

(Continued)

OTHER PUBLICATIONS

U.S. Appl. No. 13/271,744, Advisory Action mailed Mar. 24, 2014, 3 pgs.
(Continued)

*Primary Examiner* — Eduardo C Robert
*Assistant Examiner* — Steven Cotroneo
(74) *Attorney, Agent, or Firm* — Schwegman Lundberg & Woessner, P.A.

(57) ABSTRACT

A clamping device for an external fixation system includes a post component having a yaw axis, a first clamp secured to the post component and rotatable about the yaw axis, and a second clamp secured to the post component and rotatable about the yaw axis relative to the first clamp. The device includes a tightening component configured in a manner that an action of tightening the tightening component simultaneously locks both the first and second clamps in a gripping arrangement and substantially eliminates their relative rotation about the yaw axis. Interdigitating components can be spaced apart by high spring rate biasing elements that so as to allow for smooth adjustment of the clamping device components relative to each other until the appropriate position is achieved and until after a sufficiently high clamping load has been applied.

22 Claims, 27 Drawing Sheets

Related U.S. Application Data

(60) Provisional application No. 61/392,325, filed on Oct. 12, 2010, provisional application No. 61/392,298, filed on Oct. 12, 2010, provisional application No. 61/392,339, filed on Oct. 12, 2010.

(56) References Cited

U.S. PATENT DOCUMENTS

| | | | |
|---|---|---|---|
| 3,044,512 | A | 7/1962 | Jones |
| 3,154,331 | A | 10/1964 | Engelhardt |
| 3,373,465 | A | 3/1968 | Johnson et al. |
| 3,406,987 | A | 10/1968 | Hunder et al. |
| 4,037,978 | A | 7/1977 | Connelly |
| 4,115,966 | A | 9/1978 | Delee |
| 4,312,488 | A | 1/1982 | Pierron |
| 4,388,747 | A | 6/1983 | Plummer |
| 4,483,334 | A | 11/1984 | Murray |
| 4,620,533 | A | 11/1986 | Mears |
| 4,653,481 | A | 3/1987 | Howland et al. |
| 4,662,365 | A | 5/1987 | Gotzen et al. |
| 4,700,437 | A | 10/1987 | Hoshino |
| D295,725 | S | 5/1988 | Shioda |
| 4,817,897 | A | 4/1989 | Kreusel |
| 4,895,141 | A | 1/1990 | Koenman et al. |
| 5,312,405 | A | 5/1994 | Korotko et al. |
| 5,427,465 | A | 6/1995 | Sato |
| 5,624,345 | A * | 4/1997 | Graft .................. F16C 25/083 384/563 |
| 5,662,648 | A | 9/1997 | Faccioli et al. |
| 5,683,389 | A | 11/1997 | Orsak et al. |
| 5,709,681 | A | 1/1998 | Pennig |
| 5,727,899 | A | 3/1998 | Dobrovolny |
| 5,741,252 | A | 4/1998 | Mazzio et al. |
| 5,746,741 | A | 5/1998 | Kraus et al. |
| 5,752,954 | A | 5/1998 | Mata et al. |
| 5,800,548 | A | 9/1998 | Martin et al. |
| 5,827,282 | A | 10/1998 | Pennig et al. |
| 5,860,728 | A | 1/1999 | Maglica |
| 5,891,144 | A | 4/1999 | Mata et al. |
| 5,976,141 | A | 11/1999 | Haag et al. |
| 6,022,348 | A | 2/2000 | Spitzer |
| 6,080,153 | A | 6/2000 | Mata et al. |
| 6,102,911 | A | 8/2000 | Faccioli et al. |
| 6,217,577 | B1 | 4/2001 | Hofmann |
| 6,264,396 | B1 | 7/2001 | Dobrovolny |
| 6,277,069 | B1 | 8/2001 | Gray |
| 6,376,775 | B1 | 4/2002 | Leijon et al. |
| 6,386,786 | B1 | 5/2002 | Perlman et al. |
| 6,409,729 | B1 | 6/2002 | Martinelli et al. |
| 6,500,177 | B1 | 12/2002 | Martinelli et al. |
| 6,637,082 | B1 | 10/2003 | Chang |
| 6,652,523 | B1 | 11/2003 | Evrard et al. |
| 6,702,814 | B2 | 3/2004 | Walulik et al. |
| 6,716,212 | B1 | 4/2004 | Pickens |
| 6,736,775 | B2 | 5/2004 | Phillips |
| 6,887,197 | B2 | 5/2005 | Phillips |
| 7,004,943 | B2 | 2/2006 | Ferrante et al. |
| 7,048,735 | B2 | 5/2006 | Ferrante et al. |
| 7,241,071 | B2 | 7/2007 | Carraher et al. |
| 7,241,074 | B2 | 7/2007 | Thomke et al. |
| 7,261,713 | B2 | 8/2007 | Langmaid et al. |
| 7,314,331 | B1 | 1/2008 | Koros et al. |
| 7,320,556 | B2 | 1/2008 | Vagn-erik |
| 7,473,223 | B2 | 1/2009 | Fetzer |
| 7,491,008 | B2 | 2/2009 | Thomke et al. |
| 7,527,626 | B2 | 5/2009 | Lutz et al. |
| 7,562,855 | B2 | 7/2009 | Oetlinger |
| 7,588,537 | B2 | 9/2009 | Bass |
| 7,708,736 | B2 | 5/2010 | Mullaney |
| 7,744,632 | B2 | 6/2010 | Usher |
| 7,887,537 | B2 | 2/2011 | Ferrante et al. |
| 7,931,650 | B2 | 4/2011 | Winquist et al. |
| 7,938,829 | B2 | 5/2011 | Mullaney |
| 8,172,840 | B2 | 5/2012 | Mürner et al. |
| 8,187,274 | B2 | 5/2012 | Schulze et al. |
| 8,840,611 | B2 | 9/2014 | Mullaney et al. |
| 2001/0004432 | A1 | 6/2001 | Pfister |
| 2002/0037193 | A1 | 3/2002 | Gibbons et al. |
| 2002/0042613 | A1 | 4/2002 | Mata et al. |
| 2002/0061225 | A1 | 5/2002 | Boucher et al. |
| 2002/0165543 | A1 | 11/2002 | Winquist et al. |
| 2003/0149429 | A1 | 8/2003 | Ferrante et al. |
| 2005/0113831 | A1 | 5/2005 | Franck et al. |
| 2005/0119656 | A1 | 6/2005 | Ferrante et al. |
| 2006/0017566 | A1 | 1/2006 | Gauvreau et al. |
| 2006/0039750 | A1 | 2/2006 | Thomke et al. |
| 2006/0052781 | A1 | 3/2006 | Thomke et al. |
| 2006/0155276 | A1 | 7/2006 | Walulik et al. |
| 2006/0229602 | A1 | 10/2006 | Olsen et al. |
| 2006/0229603 | A1 | 10/2006 | Olsen |
| 2006/0255521 | A1 | 11/2006 | Brunner et al. |
| 2006/0271045 | A1 | 11/2006 | Hubbard et al. |
| 2006/0287652 | A1 | 12/2006 | Lessig et al. |
| 2007/0038217 | A1 | 2/2007 | Brown et al. |
| 2007/0049932 | A1 | 3/2007 | Richelsoph et al. |
| 2007/0191685 | A1 * | 8/2007 | LeVahn .............. A61B 17/0206 600/227 |
| 2007/0198012 | A1 | 8/2007 | Thomke et al. |
| 2007/0293860 | A1 | 12/2007 | Oesch et al. |
| 2008/0065068 | A1 | 3/2008 | Thomke |
| 2008/0215053 | A1 | 9/2008 | Thomke et al. |
| 2009/0036891 | A1 | 2/2009 | Brown et al. |
| 2009/0088751 | A1 * | 4/2009 | Mullaney ........... A61B 17/6466 606/59 |
| 2009/0299368 | A1 | 12/2009 | Bauer et al. |
| 2011/0098706 | A1 | 4/2011 | Mullaney |
| 2011/0098707 | A1 | 4/2011 | Mullaney |
| 2011/0172663 | A1 | 7/2011 | Mullaney |
| 2012/0004659 | A1 | 1/2012 | Miller et al. |
| 2012/0089142 | A1 | 4/2012 | Mullaney |
| 2012/0095462 | A1 | 4/2012 | Miller |
| 2012/0209264 | A1 | 8/2012 | Zandona et al. |

FOREIGN PATENT DOCUMENTS

| | | |
|---|---|---|
| EP | 2294994 A1 | 3/2011 |
| WO | WO-8905126 A1 | 6/1989 |
| WO | WO-9011055 A1 | 10/1990 |
| WO | WO-9212683 A1 | 8/1992 |
| WO | WO-9851227 A1 | 11/1998 |
| WO | WO-9925264 A1 | 5/1999 |
| WO | WO-03065911 A1 | 8/2003 |
| WO | WO-2006103087 A1 | 10/2006 |
| WO | WO-2009004347 A1 | 1/2009 |
| WO | WO-2012051312 | 4/2012 |

OTHER PUBLICATIONS

U.S. Appl. No. 13/271,744, Examiner Interview Summary mailed Apr. 21, 2014, 3 pgs.

U.S. Appl. No. 13/271,744, Final Office Action mailed Jan. 3, 2014, 13 pgs.

U.S. Appl. No. 13/271,744, Non Final Office Action mailed Jun. 5, 2013, 10 pgs.

U.S. Appl. No. 13/271,744, Notice of Allowance mailed May 15, 2014, 5 pgs.

U.S. Appl. No. 13/271,744, Preliminary Amendment filed Oct. 12, 2011, 7 pgs.

U.S. Appl. No. 13/271,744, Response filed Feb. 27, 2014 to Final Office Action dated Jan. 3, 2014, 15 pgs.

U.S. Appl. No. 13/271,744, Response filed Apr. 30, 2014 to Advisory Action mailed Mar. 24, 2014, 14 pgs.

U.S. Appl. No. 13/271,744, Response filed Sep. 5, 2013 to Non Final Office Action mailed Jun. 5, 2013, 13 pgs.

International Application Serial No. PCT/US2008/077800, International Search Report mailed Dec. 2, 2008, 4 pgs.

International Application Serial No. PCT/US2008/077800, Written Opinion mailed Dec. 2, 2008, 5 pgs.

International Application Serial No. PCT/US2011/042813, International Search Report mailed Oct. 13, 2011, 4 pgs.

(56) References Cited

OTHER PUBLICATIONS

International Application Serial No. PCT/US2011/042813, International Written Opinion mailed Oct. 13, 2011, 5 pgs.
International Application Serial No. PCT/US2011/055907, International Search Report mailed Jan. 9, 2012, 3 pgs.
International Application Serial No. PCT/US2011/055907, Written Opinion mailed Jan. 9, 2012, 5 pgs.
International Application Serial No. PCT/US2011/055980, International Preliminary Report on Patentability mailed Apr. 25, 2013, 11 pgs.
International Application Serial No. PCT/US2011/055980, International Search Report mailed Mar. 5, 2012, 5 pgs.
International Application Serial No. PCT/US2011/055980, Written Opinion mailed Mar. 5, 2012, 9 pgs.
International Application Serial No. PCT/US2011/059303, International Search Report mailed Mar. 20, 2012, 5 pgs.
International Application Serial No. PCT/US2011/059303, Written Opinion mailed Mar. 20, 2012, 7 pgs.
International Application Serial No. PCT/US2011/063976, International Search Report mailed Apr. 10, 2012, 3 pgs.
International Application Serial No. PCT/US2011/063976, Written Opinion mailed Apr. 10, 2012, 3 pgs.
International Application Serial No. PCT/US2011/963985, International Search Report mailed Mar. 28, 2012, 5 pgs.
International Application Serial No. PCT/US2011/963985, Written Opinion mailed Mar. 28, 2012, 5 pgs.
Swiss Application Serial No. 03891906, Application filed Dec. 16, 1991, Swiss Patent Office, "Fixateur externe," Applicant—Jaquet Orthopedie S. A., (Dec. 16, 1991), 34 pgs.
European Application Serial No. 11773954.0, Communication Pursuant to Article 94(3) EPC mailed Mar. 16, 2016, 4 pgs.
European Application Serial No. 11773954.0, Response filed Dec. 13, 2013 to Communication pursuant to Rules 161(1) and 162 EPC mailed Jun. 3, 2013, 7 pgs.
European Application Serial No. 11773954.0, Response filed Jul. 26, 2016 to Communication Pursuant to Article 94(3) EPC mailed Mar. 16, 2016, 4 pgs.

* cited by examiner

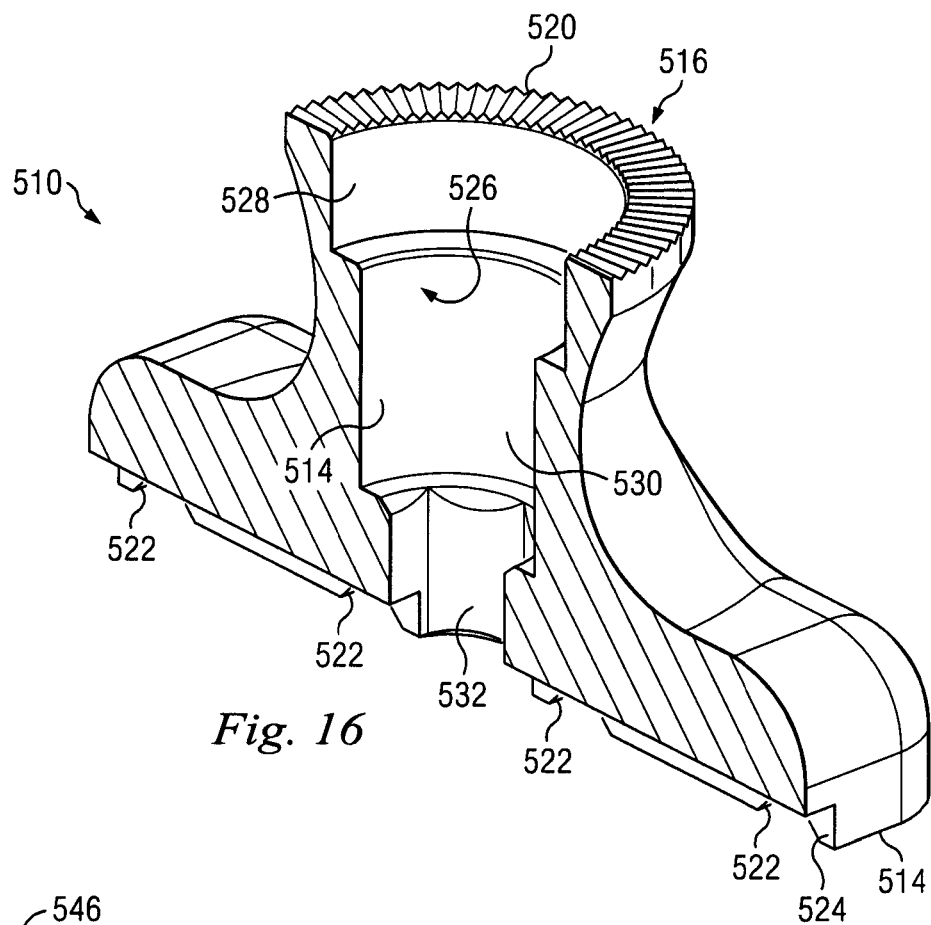
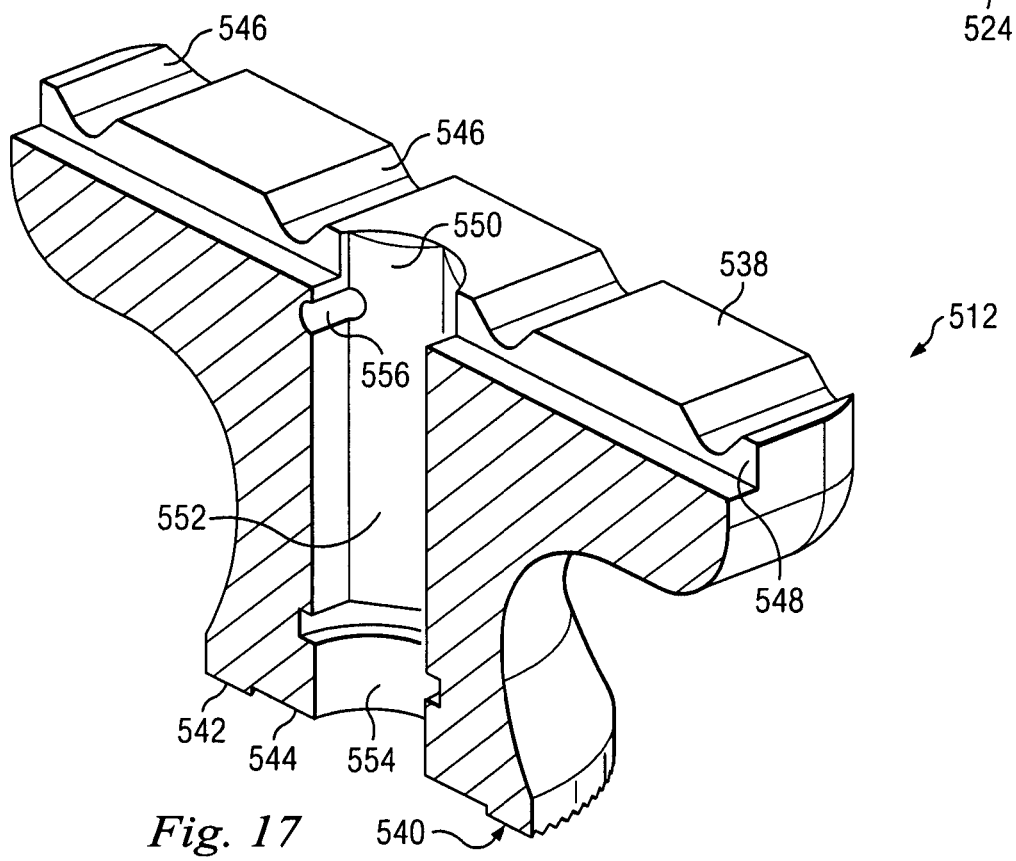
*Fig. 16*
*Fig. 17*

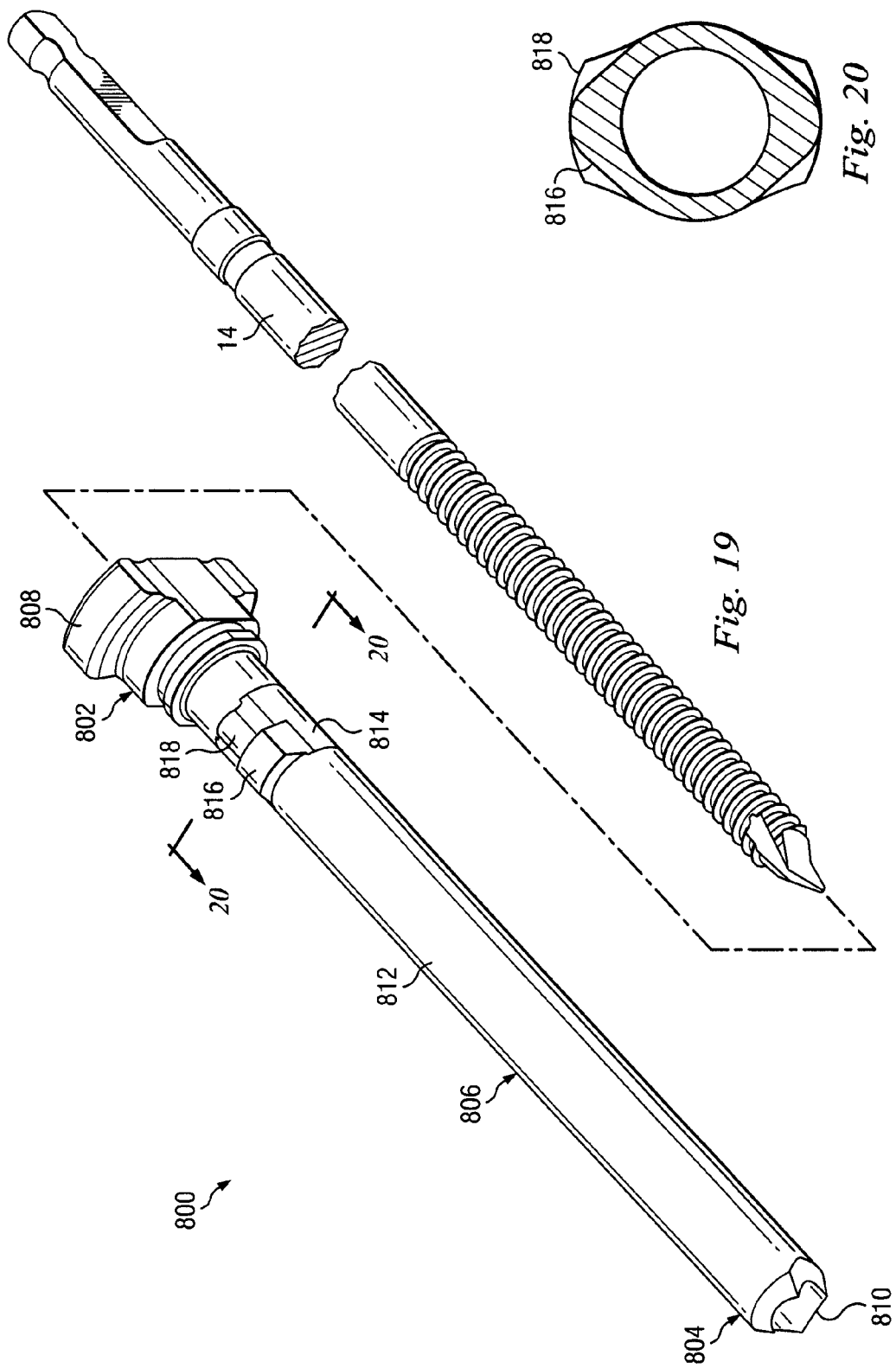

SINGLE LOCK EXTERNAL FIXATION CLAMP ARRANGEMENT AND METHOD

PRIORITY

This application is a continuation of U.S. patent application Ser. No. 13/271,744, titled Single Lock External Fixation Clamp Arrangement and Method, filed Oct. 12, 2011, which claims priority to U.S. Provisional Patent Application 61/392,325, titled Single Lock External Fixation Clamp Arrangement and Method, filed Oct. 12, 2010, U.S. Provisional Patent Application 61/392,298, titled Locking Tissue Protector, filed Oct. 12, 2010, and U.S. Provisional Patent Application 61/392,339, titled External Fixation System clamp with High Spring Rate Biasing Elements, filed Oct. 12, 2010, all of which are incorporated herein by reference.

FIELD OF THE INVENTION

This application is directed to external bone fixation systems, devices, and methods.

BACKGROUND

External fixation systems are used to stabilize fractured bones or hold bones after corrective surgery. They are usually made up of structural members held together by clamps, all assembled by the surgeon during surgery. The clamps are placed on bone pins and are attached to bars, creating a frame to hold the bones in particular relationships. Typically, the external fixation frame is assembled in the configuration the surgeon desires, then the fracture is reduced and the clamps are tightened.

Multi-pin clamps, a common type of component of external fixation systems, are configured to hold two or more bone pins. Typically, these multi-pin clamps include posts that are connected to other fixation system components, such as bars, by separate clamping devices. Some known multi-pin clamps and some known separate clamping devices each have two bolts used to connect them to the other fixation system components. When assembling an external fixation system, this can result in six bolts that need to be tightened. Other known multi-pin clamps have built-in bar clamps or bar clamps that are directly attached to them. These typically don't have the flexibility of positions provided by using an independent clamping device, but they are frequently less costly. These typically have four to six bolts that need to be tightened to lock the fixation system in the final position. Either method often requires that a number of connections are tightened to lock the multi-pin clamp to the pins and to the rest of the external fixation system. Individually tightening these multiple connections can be time consuming and can be confusing and distracting in the operating room.

Furthermore, if the system employs protective sleeves during placement, the problem of adjusting a large number of bolts is compounded. Protective sleeves are used to limit damage to soft tissue caused as the pin is advanced to or screwed into the bone. Protective sleeves are also used as guides where the multi-pin clamps have specific locations for the pins to fit relative to other pins. One common method for maintaining the position of one pin relative to another is to have a protective sleeve guide that holds the pins in a particular relationship to each other while they are driven into bone. Another method includes holding the protective sleeves in the clamps themselves in the same slots that will hold the pin. When using the clamp and a protective sleeve, the clamp has to be tightened onto the sleeves to keep it from slipping and to allow the easy transfer of force from the surgeon to the sleeves. However, both of these methods can create inefficiencies. When using a separate guide, the surgeon has to remove the guide, obtain the clamp, manipulate the clamp over the pins in the proper orientation, and then tighten the clamp onto the pins. The advantage of using the definitive clamp along with protective sleeves is that the clamp can be loosened, the sleeves can be removed from the clamp and the clamp tightened on the final pins without having to relocate the clamp over the pins. The disadvantage is that the surgeon has to provisionally tighten the clamp, typically using a separate wrench for this, then loosen the clamp and retighten it after the pins are placed, again requiring individual loosening and tightening of connections.

As described above, the fixation frame is typically assembled first, then the fracture is reduced. During this reduction phase, the bars and pins may slide in the clamps and the clamps may rotate to the final desired position. In order to maintain rigidity when the clamps are in the final position, some clamps use features that interdigitate with other features. While reducing the fracture, the interdigitating components are typically loosely held together, permitting the components to rotate relative to each other, jumping on the interdigitating features. However, to hold the rods and the pins snugly for final adjustment, the clamps are usually tightened to a load that exceeds the spring force separating the interdigitating features. This makes further adjustment of the fixation system difficult when the rods and pins are snugly held.

For example, helical wire springs that fit into conventional external fixation system clamps have spring rates that range from less than 1 pound per inch to higher than 20 pounds per inch. Loads that completely close the springs are in the single or low double digits. Typical loads achieved by finger tightening are more on the order of 100 to 200 pounds. This means the springs compress and interdigitating components completely come together well before the user can generate any significant clamping load on the pins or rods. If the surfaces have features that interdigitate with each other, adjustment of the clamp once some clamping load has been applied can be difficult, with the components catching and jumping when adjusted.

The system of the present disclosure is directed to overcoming one or more of the shortcomings of prior devices.

SUMMARY

In one exemplary aspect, the present disclosure is directed to a multi-pin clamp with built-in bar clamps that can be tightened to the pins and to the bars by tightening only one component.

In one exemplary aspect, the present disclosure is directed to a clamping device for an external fixation system. The clamping device includes a post component having a yaw axis and includes a first clamp secured to the post component and rotatable about the yaw axis. A second clamp is secured to the post component and is rotatable about the yaw axis relative to the first clamp. An intervening member is disposed between and separates the first clamp and the second clamp. A tightening component is associated with the first clamp and configured in a manner such that an action of tightening the tightening component simultaneously locks both the first and second clamps and locks their rotation about the yaw axis.

In one example, a second tightening component is associated with the second clamp, and each of the first and second tightening components are configured in a manner that an action of tightening one of the tightening components simultaneously locks both the first and second clamps.

In another exemplary aspect, the present disclosure is directed to a clamping device for an external fixation system that includes a post component having a yaw axis and a first clamp secured to the post component and rotatable about the yaw axis. A second clamp is secured to the post component and is rotatable about the yaw axis relative to the first clamp. The system includes a third clamp secured to the post component and rotatable about the yaw axis relative to the first and second clamps, and includes a tightening component configured in a manner that an action of tightening the tightening component simultaneously locks all three clamps and locks their rotation about the yaw axis.

In another exemplary aspect, the present disclosure is directed to an external fixation system, including a clamp configured to grip two or more bone engaging fixation elements and a protective sleeve configured to align the bone engaging fixation elements during insertion into bone, the sleeve being structurally arranged to cooperate with the clamp to lock the sleeve in position relative to the clamp to prevent sliding along the long axis of the bone engaging fixation element. In one aspect, the sleeve comprises a flange portion configured to mechanically interfere with the clamp and prevent sliding along the long axis of the bone engaging fixation element.

In another exemplary aspect, the present disclosure is directed to an external fixation system including a clamp configured to grip two or more bone engaging fixation elements and a protective sleeve configured to fit into the clamp. The sleeve is configured to guide an external fixation pin during pin insertion. In one aspect, the protective sleeve includes a flange that mechanically interferes with the clamp to prevent the sleeve from sliding along the long axis of the pin when force is applied in an axial direction.

In another exemplary aspect, the present disclosure is directed to an external fixation system, including a clamp configured to hold a plurality of bone fixation pins. The clamp includes a first jaw configured to interface with the bone fixation pins and includes a second jaw configured to interface with the bone fixation pins. The first and second jaws are arranged to cooperatively capture the bone fixation pins. The clamp also includes a locking element configured to lock the first and second jaws in a clamping condition and includes a biasing element biasing the first and second jaws towards each other. The biasing element is arranged to provide an initial clamping load onto the bone fixation pins prior to locking with the locking elements. The system includes a protective sleeve disposable between the first an second jaws. The protective sleeve is sized to receive the bone fixation pin and has a diameter large enough to displace one of the first and second jaws and at least partially compress the biasing element.

In another exemplary aspect, the present disclosure is directed to a method including the steps of placing a protective sleeve within a clamp of an external fixation clamping device so that a protruding feature on the sleeve engages the clamp and mechanically prevents axial displacement of the sleeve in an axial direction, inserting the sleeve into a patient's surgical site, and driving a bone engaging fixation element through the sleeve, the sleeve forming a barrier between the bone fixation element and soft tissue.

In another exemplary aspect, the present disclosure is directed to a protective sleeve for separating tissue from a bone-engaging fixation element. The sleeve includes a hollow body having a first end region and a second end region. The body is sized to be held by an external fixation clamp, and has a clamp interfacing portion arranged to cooperate with the external fixation clamp to mechanically prevent axial displacement in the clamp. The sleeve also includes a projecting graspable portion disposed at the second end region. In one aspect, the sleeve includes a flange portion configured to mechanically interfere with the clamp and prevent axial sliding.

In another exemplary aspect, the present disclosure is directed to an adjustable clamping device for an external fixation system. The system includes a clamp for grasping an external fixation element, where the clamp includes a first interdigitating surface. An adjacent component moves relative to the clamp and has a second interdigitating surface configured to engage the first interdigitating surface of the clamp and lock the orientation of the clamp relative to the adjacent component. A first biasing element has a high spring rate configured to space the first and second interdigitating features apart so as to allow for smooth adjustment of the clamp until the appropriate position is achieved and until after a sufficiently high clamping load has been applied.

In one aspect, the adjacent component is a second clamp. In one aspect, the adjacent component is a base component.

In another exemplary aspect, the present disclosure is directed to a clamping device for an external fixation system that includes a first outer jaw, a first inner jaw, and a first biasing element for biasing the first outer and first inner jaws in an open position for receiving a first external fixation element. The first inner jaw includes radial splines configured to interdigitate and restrict motion. The clamping device also includes a second outer jaw, a second inner jaw and a second biasing element for biasing the second outer and second inner jaws in an open position for receiving a second external fixation element. The second inner jaw has radial splines configured to interdigitate and restrict motion. A high spring rate biasing element is configured to maintain separation of the splines until a sufficiently high clamping load has been applied. I one aspect, the first and second biasing elements each have a spring rate lower than the spring rate of the high spring rate biasing element.

In another exemplary aspect, the present disclosure is directed to a clamping device for an external fixation system. The clamping device includes a first outer jaw, a first inner jaw, and a first biasing element for biasing the first outer and first inner jaws in a closed position for receiving a first external fixation element. The first inner jaw has radial splines configured to interdigitate and restrict motion. The clamping device also includes a second outer jaw, a second inner jaw and a second biasing element for biasing the second outer and second inner jaws in a closed position for receiving a second external fixation element. The second inner jaw has radial splines configured to interdigitate and restrict motion. A high spring rate biasing element is configured to maintain separation of the splines until a sufficiently high clamping load has been applied.

In another exemplary aspect, the present disclosure is directed to a clamping device for an external fixation system. The clamping device includes an outer jaw and an inner jaw, a lower spring rate biasing element for biasing the orientation of the inner and outer jaw relative to each other, and a base component having a concave surface interfacing with the first inner jaw and an opposing bottom facing surface. The concave surface being configured for selective engagement with the matching surface of the first inner jaw. A higher spring rate biasing element is interposed between the first inner jaw and the base component to maintain separation of the splines until a sufficiently high clamping load has been applied.

In another exemplary aspect, the present disclosure is directed to a clamping device that includes a first component having a first surface having first friction enhancing features and includes a second component having a second surface having second friction enhancing features. The second component is rotatable relative the first component about an axis, and the second friction enhancing features are disposed to selectively engage with the first friction enhancing features when sufficient load is applied. A first biasing element is disposed between the first and second components and separates the first and second surfaces. The first biasing element maintains separation of the first and second surfaces until at least 50 pounds of load has been applied.

In yet another exemplary aspect, the present disclosure is directed to an adjustable clamping device for an external fixation system. The clamping device comprises a clamp configured to grasp an external fixation element, the clamp comprising a first interdigitating surface. The clamping device also includes a component moveable relative to the clamp and having a second interdigitating surface configured to engage the first interdigitating surface and lock the orientation of the clamp relative to the component. A first biasing element having a lower spring rate biases the clamp and component to affect the frictional forces holding the clamp and component relative to one another. A second biasing element having a higher spring rate spaces the interdigitating features apart so as to allow for smooth adjustment of the clamp relative to the component.

In another exemplary aspect, the present disclosure is directed to an adjustable clamping device for an external fixation system. The device includes a clamp configured to grasp an external fixation element, the clamp including a first interdigitating surface. An external fixation component is moveable relative to the clamp and has a second interdigitating surface configured to engage the first interdigitating surface and lock the orientation of the clamping device relative to the other external fixation component. A first biasing element has a spring rate selected to allow for some mechanical overlap of interdigitating features in a manner permitting clicking during movement of the clamping device relative to the external fixation component.

In one exemplary aspect, the present disclosure is directed to a clamping device for an external fixation system that includes a post component having a yaw axis, a first clamp secured to the post component and rotatable about the yaw axis, and a second clamp secured to the post component and rotatable about the yaw axis relative to the first clamp. Some embodiments incorporate additional clamps interposed between the first and second clamps, secured to the post component and rotatable about the yaw axis. The device includes a tightening component configured in a manner that an action of tightening the tightening component simultaneously locks all clamps in a gripping arrangement and substantially eliminates their rotation about the yaw axis. In some examples, the tightening component comprises a first tightening component associated with the first clamp and a second tightening component associated with the second clamp. Each of the first and second tightening components may be configured in a manner that an action of tightening one of the tightening components simultaneously locks both the first and second clamps.

In one another exemplary aspect, the present disclosure is directed to a tissue protector that includes protective sleeves and a clamp arranged to protect tissue while reducing the number of steps that need to be taken during a procedure. The protective sleeve may be locked in the clamp quickly and in such a manner that the surgeon can put a load on the clamp to hold the sleeve against the bone. Friction force may hold the clamp in position relative to the pin or protective sleeve without the need to tighten clamping bolts.

In one exemplary aspect, the present disclosure is directed to an external fixation system clamping device that has added biasing components with high spring rates so that high forces can be applied to the clamping elements while still allowing smooth adjustment of the clamp position. Accordingly, instead of having interdigitating features that catch and jump when adjusted as described above, the present disclosure is directed to a system that reduces or eliminates interference between interdigitating features until the interdigitating features are intended to be engaged with each other. Using a properly sized spring washer, the surfaces intended to interdigitate with each other can be kept apart while the frictional loads between the fixation elements and the clamp can be increased. This makes the adjustment of the relative positions of the different clamp components a smoother operation.

In one exemplary aspect, the present disclosure is directed to an adjustable clamp for an external fixation system that includes a clamping device for grasping an external fixation element. The clamping device includes a first interdigitating surface. The adjustable clamp also includes an external fixation component moveable relative to the clamping device and having a second interdigitating surface configured to engage the first interdigitating surface and lock the orientation of the clamping device relative to the other external fixation component. The adjustable clamp comprises a first biasing element having a lower spring rate configured to bias clamping device components to affect the frictional forces holding the components relative to one another, and the adjustable clamp comprises a second biasing element having a higher spring rate configured to space the interdigitating features apart so as to allow for smooth adjustment of the clamping device components relative to each other until the appropriate position is achieved and until after a sufficiently high clamping load has been applied.

Some components of the clamp may be similar in some respects to components found in U.S. Patent Application Publication No. 2009/0088751 to Mullaney, application Ser. No. 12/238,532, incorporated herein by reference, or may be similar in some respects to components found in U.S. patent application Ser. No. 13/175,343, titled Multi-Locking External Fixation Clamp, filed Jul. 1, 2011, incorporated by reference herein in its entirety.

BRIEF DESCRIPTION OF THE DRAWINGS

Aspects of the present disclosure are best understood from the following detailed description when read with the accompanying figures.

FIG. 16 is an illustration of a cross-sectional view of an exemplary pin jaw of the clamping device of FIG. 13 in accordance with one exemplary aspect of the present disclosure.

FIG. 17 is an illustration of a cross-sectional view of another exemplary pin jaw of the clamping device of FIG. 13 in accordance with one exemplary aspect of the present disclosure.

FIG. 19 is an illustration of an exemplary protective sleeve and pin assembly usable with the clamping device of FIG. 13 in accordance with one exemplary aspect of the present disclosure.

FIG. 20 is an illustration of a cross-sectional view of the sleeve of FIG. 19.

DETAILED DESCRIPTION

Figure 1:
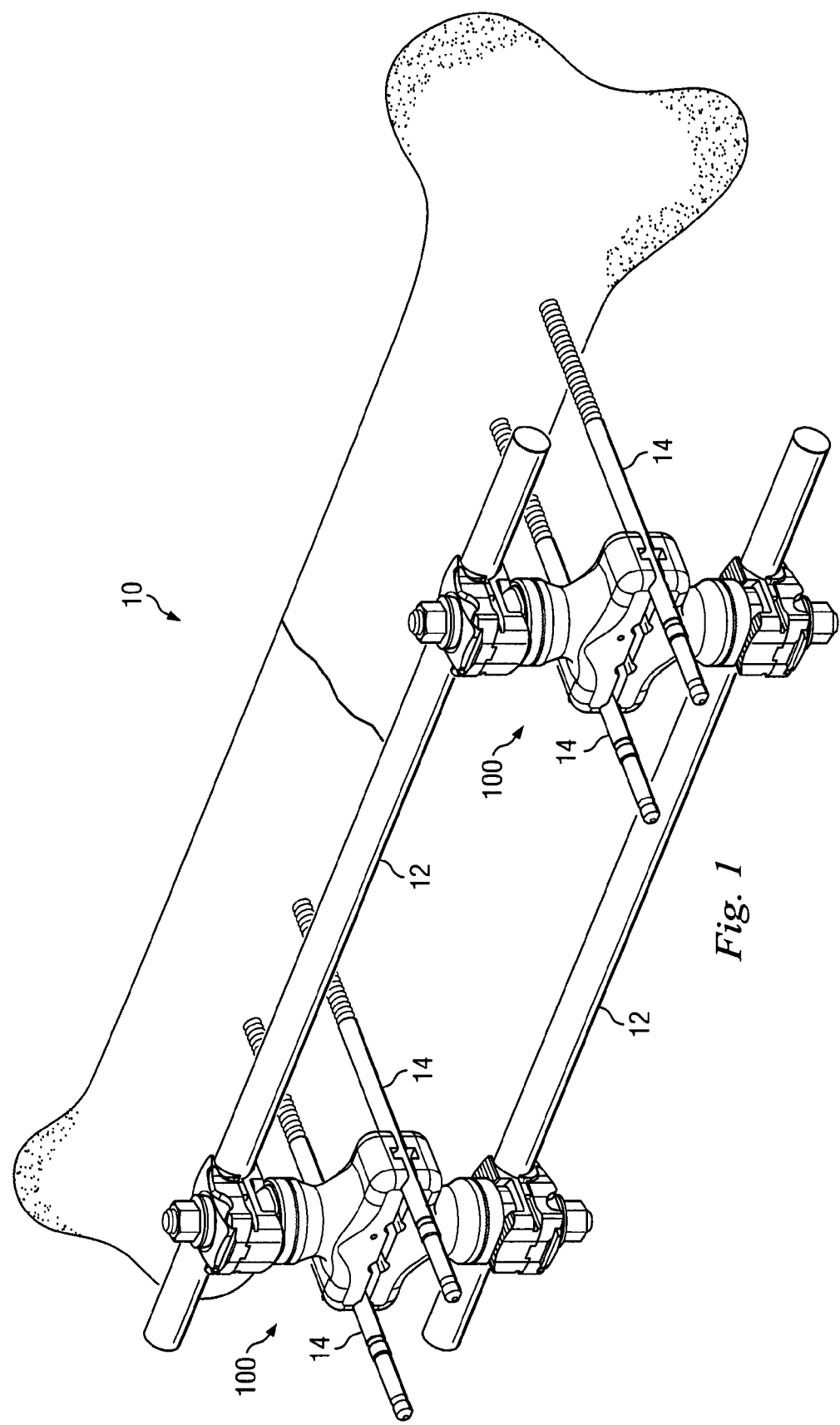
FIG. 1 is an illustration of an exemplary external fixation system in accordance with one exemplary aspect of the present disclosure connected to a long bone.

The present disclosure relates generally to the field of external fixation systems, and more particularly to clamping devices for connecting bone pins, wires, rings, struts, bars, rods, or promoting an understanding of the principles of the invention, reference will now be made to embodiments or examples illustrated in the drawings, and specific language will be used to describe these examples. It will nevertheless be understood that no limitation of the scope of the invention is thereby intended. Any alteration and/or further modifications in the described embodiments, and any further applications of the principles of these inventions as described herein are contemplated as would normally occur to one skilled in the art to which the disclosure relates.

The external fixation system disclosed herein provides multiple advantages over prior systems. For example, it includes a clamping device having a plurality of clamps, including end clamps arranged to receive and secure fixation rods or bars (or other fixation elements) and including a pin clamp arranged to receive and secure bone pins (or other bone engaging fixation elements) that extend into and secure patient tissue. These multiple clamps, however, are arranged, in at least one aspect, to be all tightened through a single input. This increases simplicity and efficiency of fixation system setup, producing less work for surgeons and is less disruptive in the operating room.

FIG. 1 shows an exemplary external fixation system 10 attached to a fractured long bone. The system 10 includes rigid bars 12 and plurality of pins 14 drilled into the bone on opposing sides of the fracture. Although this disclosure references bars and pins, it should be understood that any fixation element may be used, including bone pins, wires, rings, struts, bars, rods, or other structural members. A clamping device 100 connects each pin 14 to the bars 12 for rigid fixation and traction. In the example in FIG. 1, each pin 14 is received into one of the clamping devices 100 by inserting the pin 14 between facing pin jaws of a fixator pin clamp of the clamping device 100 as is described further below. Likewise, each bar 12 is received into one of the clamping devices 100 by inserting the bar 12 between open inner and outer jaws of a fixator bar clamp of the clamping device 100 as is described further below, to establish the external fixation framework for bone stabilization. In some embodiments, inserting the bar 12 triggers the fixator clamp to change from an open position to a provisionally locked position about the bar 12. In this position, the fixator bar clamp can be rotated about the bar 12 and may be axially displaced along the bar 12. In addition, it may rotate about a longitudinal axis of the clamping device, and it may pitch up or down around the cylindrical axis of a saddle element, but the jaws maintain the bar in the clamp. As remaining pins 14 are connected to the bar 12 using one of the clamping devices 100, the clamping devices may be adjusted to provide angulation and orientation necessary to align the bone for healing. Additional bar-to-bar fixation components and/or bar-to-pin fixation components may be added to expand and connect the frame as required. Once properly created, the frame may be locked by changing the clamp from the provisionally locked condition to the locked condition.

FIGS. 2-5 show an exemplary embodiment of a clamping device 100 according to one exemplary aspect of the present disclosure. For convenience in FIGS. 2-5, similar components are labeled with the same reference number, but are distinguished by a suffix, with the suffix "a" identifying components of one clamp and the suffix "b" identifying components of a similar, but separate clamp. References to those components may be made without the use of the suffix.

The exemplary clamping device 100 includes three clamps, including first and second bar clamps 102a, 102b disposed at ends of the clamping device 100, and a pin clamp 104 more centrally disposed between the bar clamps 102, 102b configured to connect to fixation elements such as a bone pin, screw, or other fixation element attachable to a bone segment. Saddle assemblies 106a, 106b are disposed between the pin clamp 104 and the bar clamps 102a, 102b. Each clamp 102, 104 independently receives and secures a bar, pin or other fixation element. Other embodiments of the clamping device 100 include only a single bar clamp on one end, with a multi-clamp set or other arrangement on the other end.

Figure 2:
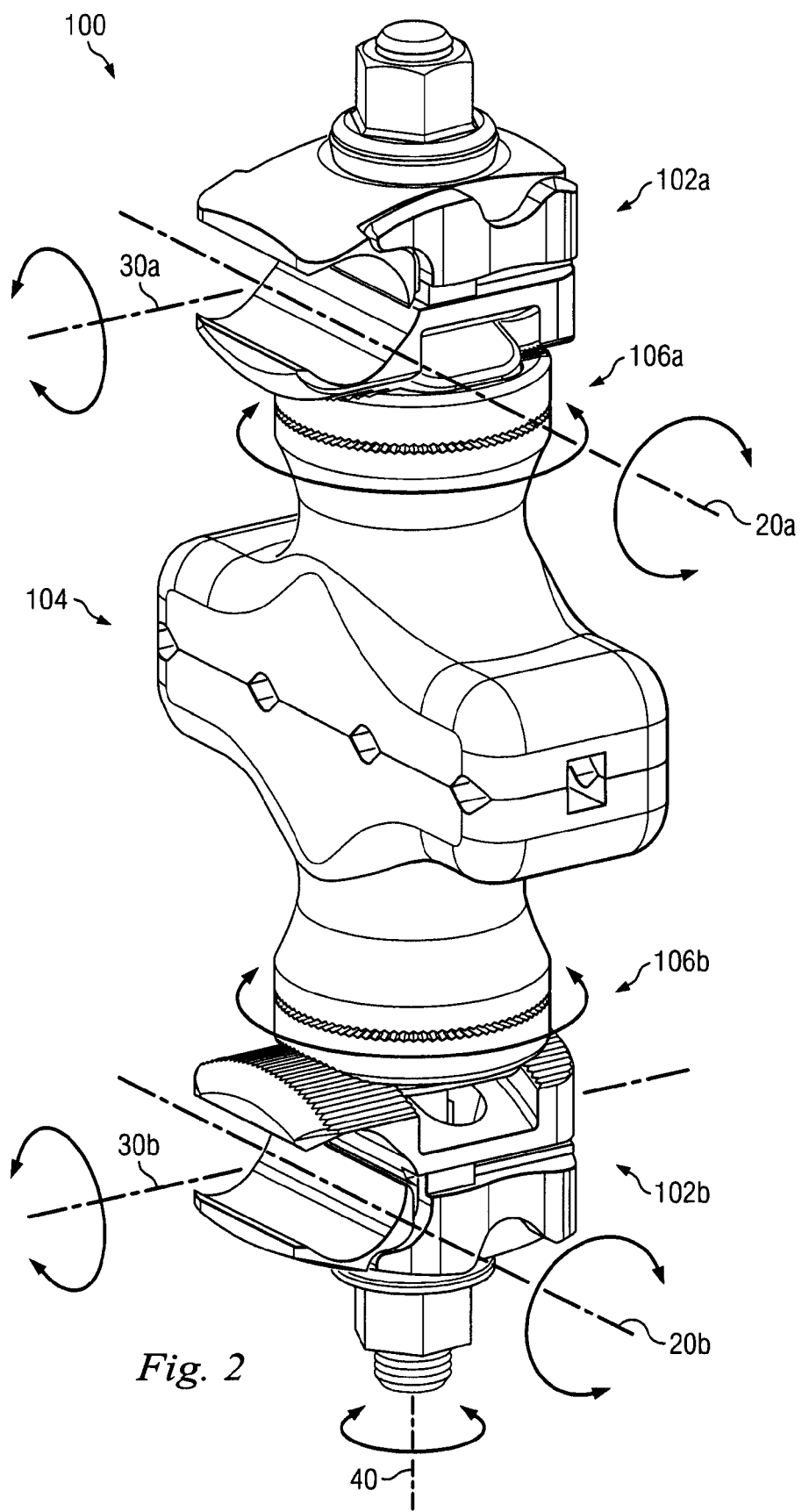
FIG. 2 is an illustration of a clamping device from the external fixation system of FIG. 1 in accordance with one exemplary aspect of the present disclosure.

As can be seen, the bar clamps 102a, 102b of the clamping device 100 provide multiple degrees of freedom, each operating independently of the other, relative to the pin clamp 104. FIG. 2 shows the degrees of freedom as a roll axis 20, a pitch axis 30, and a yaw axis 40 in the bar clamps 102. The roll axis 20 is the axis of a bar within the clamps and about which the clamping device 100 may rotate. The pitch axis 30 is the axis about which the outer and inner jaws rotate relative to the saddle assembly 106 and the rest of the clamping device. The yaw axis 40 is defined by a post component or stud (described below) and about which the clamps 102 can rotate relative to the pin clamp 104 and relative to each other.

Figure 3:
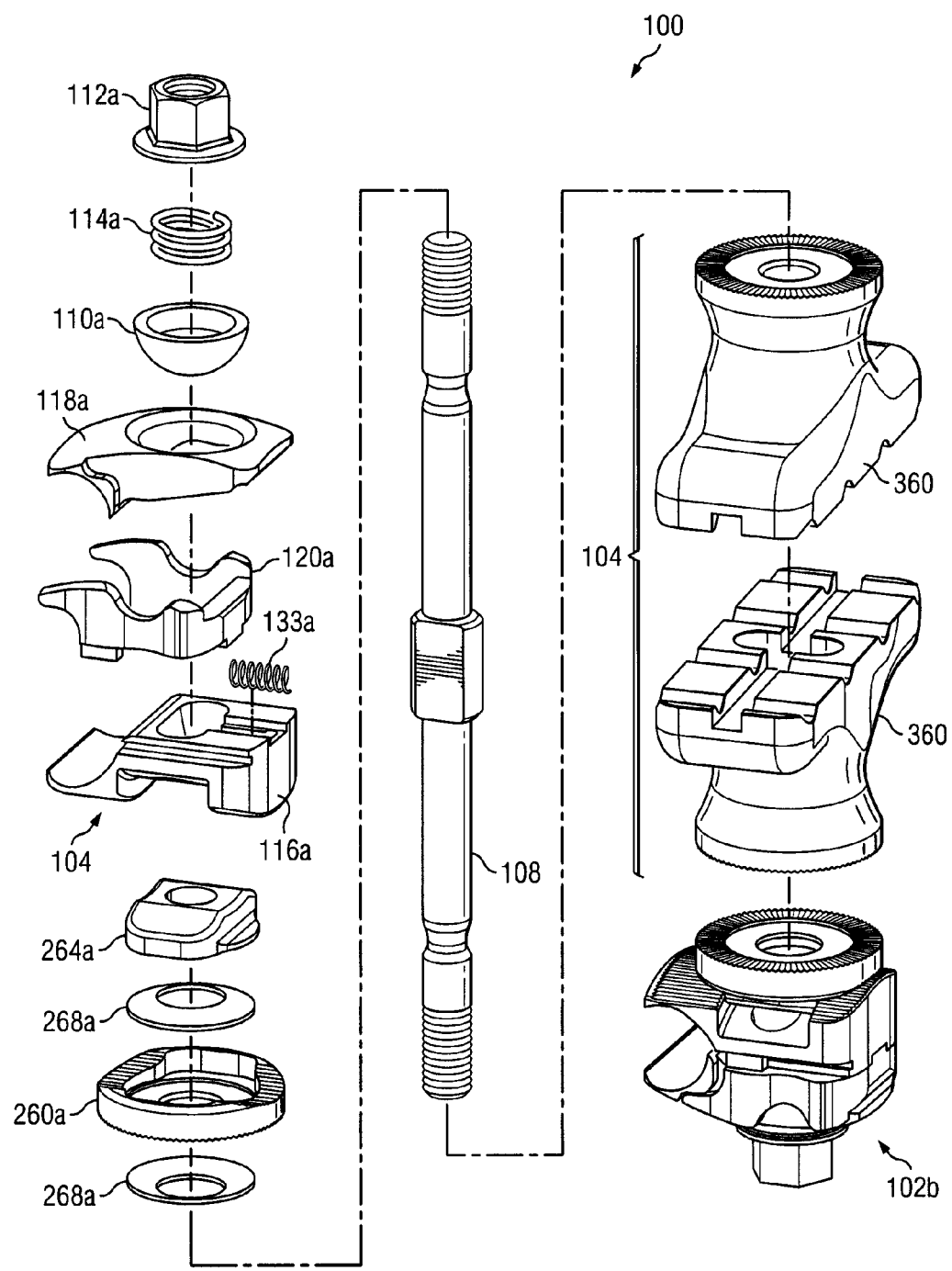
FIG. 3 is an illustration of a partial exploded view of the clamping device of FIG. 2.
Figure 4:
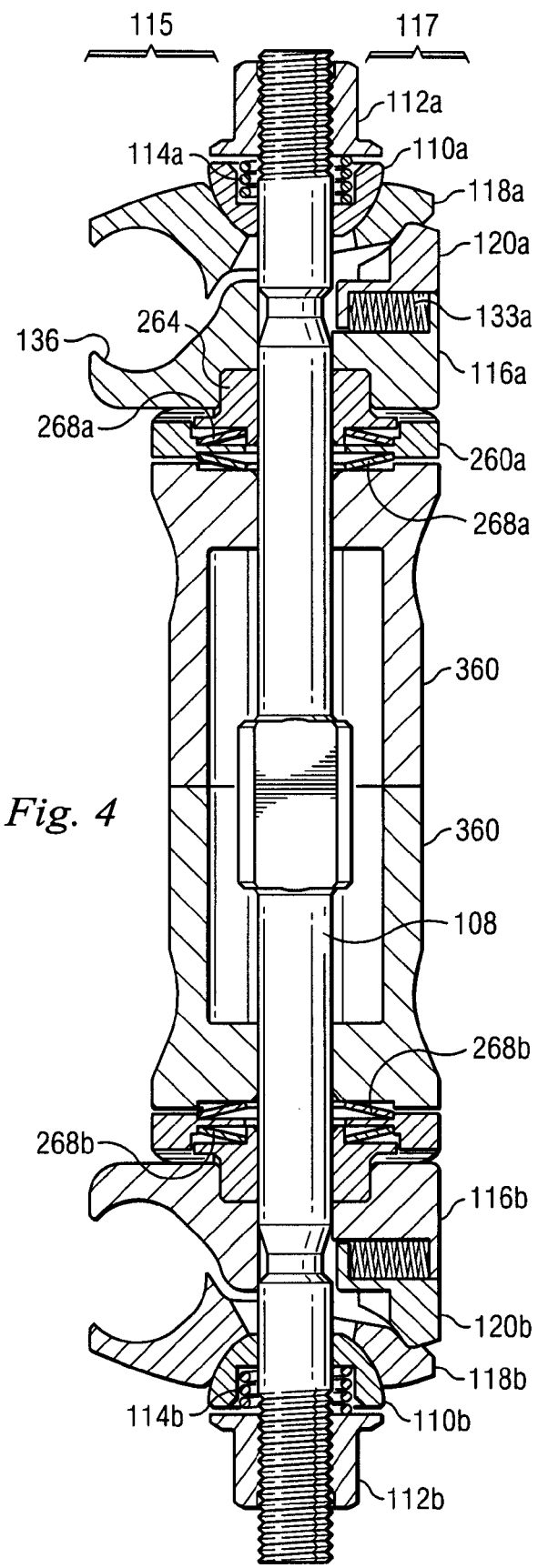
FIG. 4 is an illustration of a cross-sectional view of the clamping device of FIG. 2.
Figure 5:
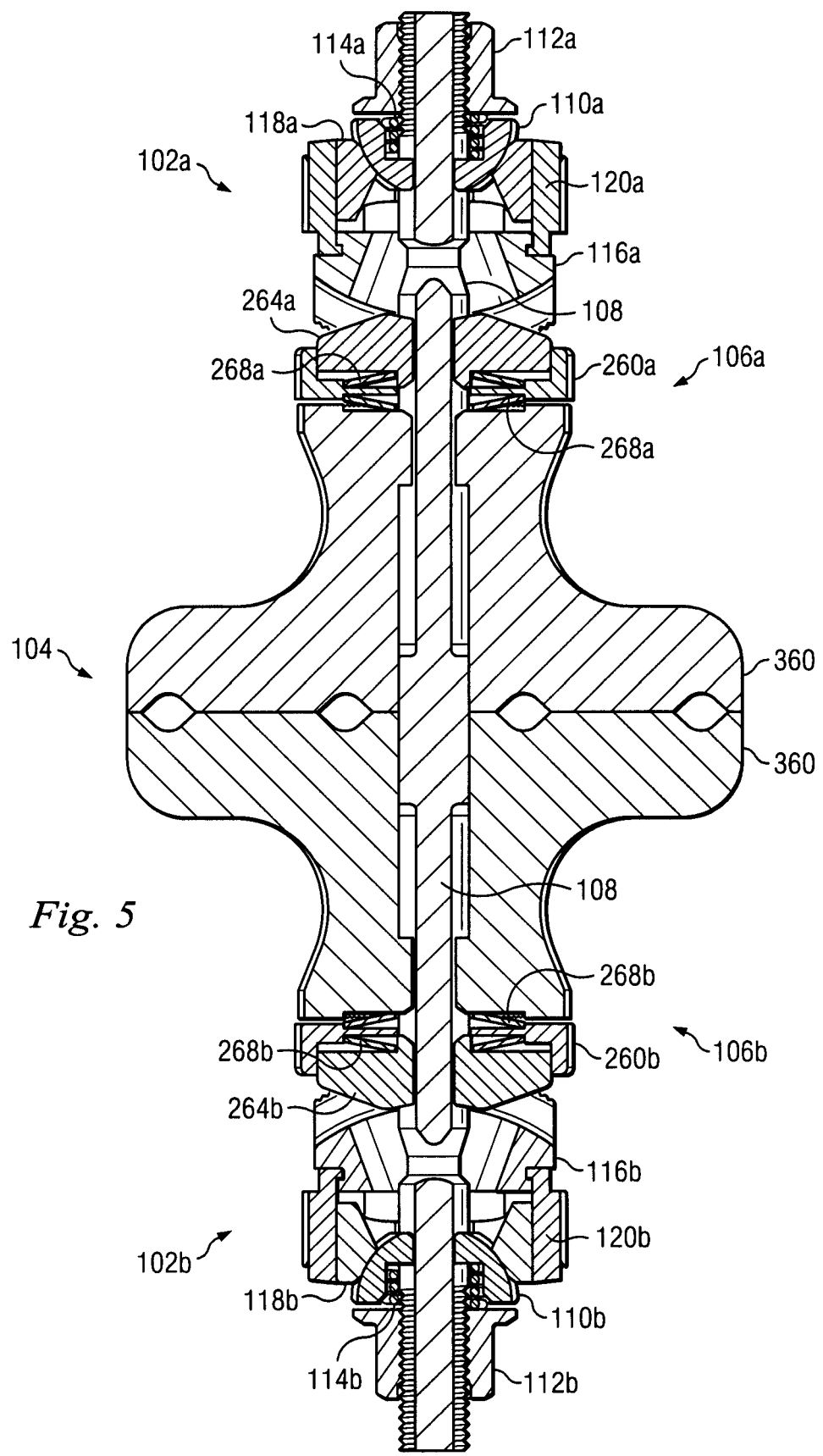
FIG. 5 is an illustration of a cross-sectional view of the clamping device of FIG. 2 taken transverse to the cross-sectional view in FIG. 4.

FIG. 2 shows an isometric view and FIG. 3 shows an exploded view, respectively, while FIGS. 4 and 5 show cross-sectional views of the clamping device 100. Referring to FIGS. 2-3, in addition to the clamps 102, 104 and saddle assemblies 106, the clamping device 100 includes a post component or stud 108, spherical washers 110, and tightening components, disclosed as nuts 112. Biasing elements, shown here as biasing springs 114 are disposed about the stud 108 between the spherical washers 110 and the nuts 112. The stud 108 extends centrally through the clamping device 100 and divides the device into a clamping side 115 representing the side of the device where fixation elements are held and introduced, and a rearward side 117 representing the side of the device opposite the clamping side 115, as shown in FIG. 4.

In the embodiment shown, and as indicated above, the rod clamps 102a, 102b are similar to each other in most respects. Therefore, to avoid duplicity and for ease of understanding, the references numbers provided in the following discussion may not include the suffix, with the understanding that equivalent or identical elements are provided on both clamps 102a, 102b. The rod clamps 102 include an inner jaw 116, an outer jaw 118, and a latch 120. The latch 120 operates to allow the rod clamps 102 to open and operates to provisionally lock the clamps 102 upon receipt of a fixation element.

Details and operation of the rod clamps 102 can be understood by referring to incorporated U.S. patent application Ser. No. 13/175,343 filed Jul. 1, 2011. However, for completeness, some descriptive subject matter relating to the clamps 102 is provided below.

FIGS. 6A-6D show various views of the inner jaw 116. The inner jaw 116 cooperates with the outer jaw 118 to clamp onto and secure a rod, bar or other external fixation element. The inner jaw 116 includes an inner clamp face 124 that faces toward the outer jaw 118 and an outer clamp face 126 that interfaces with the saddle assembly 106. It also includes a central bore 128, a saddle assembly receiving area 130, and a latch race or guide 132.

The inner clamp face 124 includes a body surface portion 134 and a gripping surface portion 136 shown as a transverse groove. In the example shown, the body surface portion 134 and the gripping surface portion 136 are vertically offset. The body surface portion 134 is disposed generally toward the rearward side 117 (FIG. 4) of the clamping device 100 and the gripping surface portion 136 is disposed at the clamping side 115 (FIG. 4) of the clamping device 100. The body surface portion 134 includes an alignment groove 135 and a biasing channel 137 formed in the groove 135 that is sized and configured to maintain a biasing member (shown as biasing member 133 in FIGS. 3 and 4), such as a spring therein. As will be explained below, the biasing channel 137 is shaped to receive the biasing member 133a, but also receives a downwardly extending tab on the latch 120 so that the biasing member 133 presses on the back of the biasing channel 137 and biases the latch 120 in the direction of the gripping surface portion 136 of the inner clamp face 124. The alignment groove 135 serves as a guide that permits passage of a corresponding element on the latch 120.

Figure 6A:
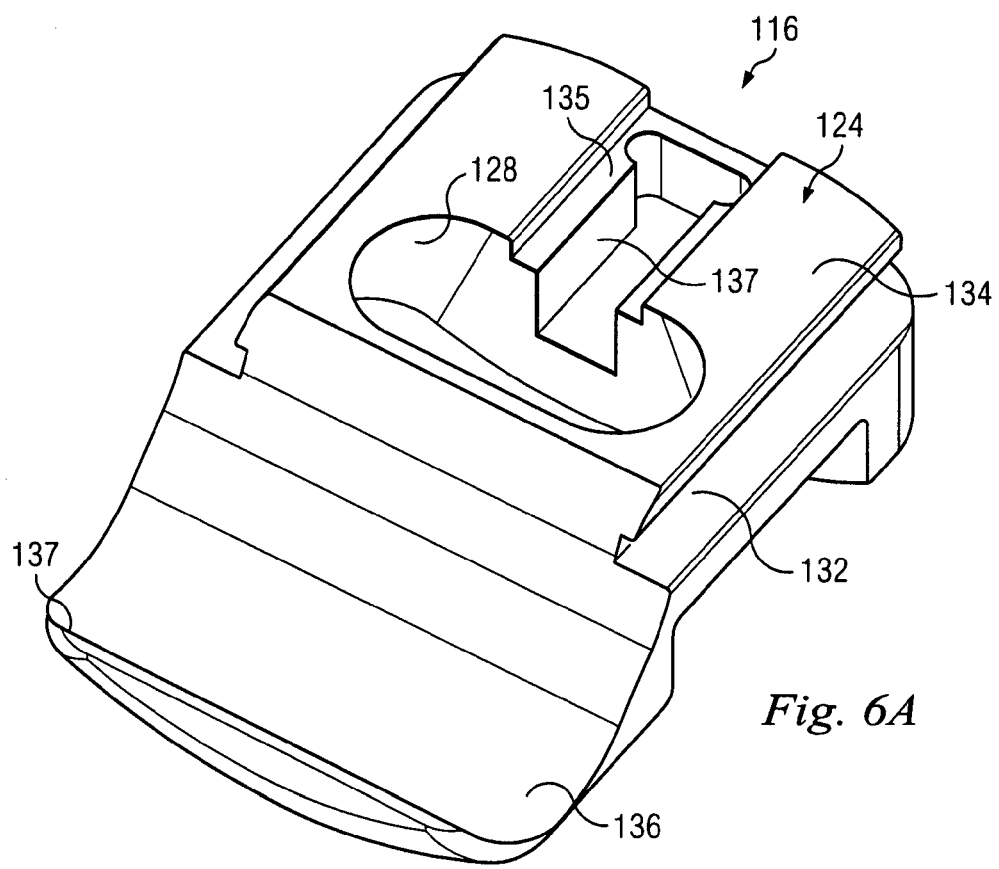
FIGS. 6A-6D are illustrations of an exemplary inner jaw of the clamping device in FIG. 2 in accordance with one exemplary aspect of the present disclosure.
Figure 6B:
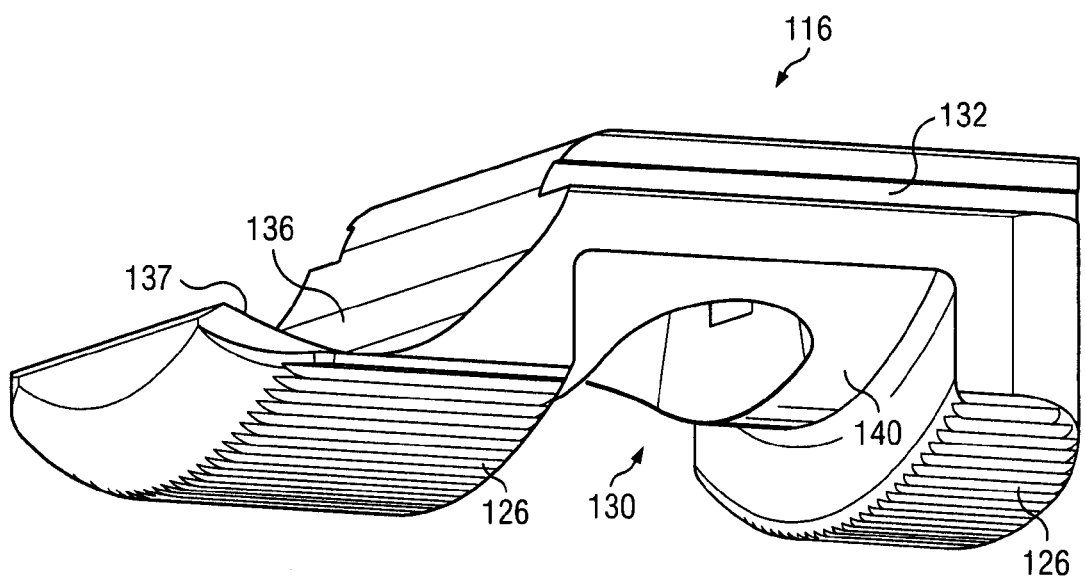
Figure 6C:
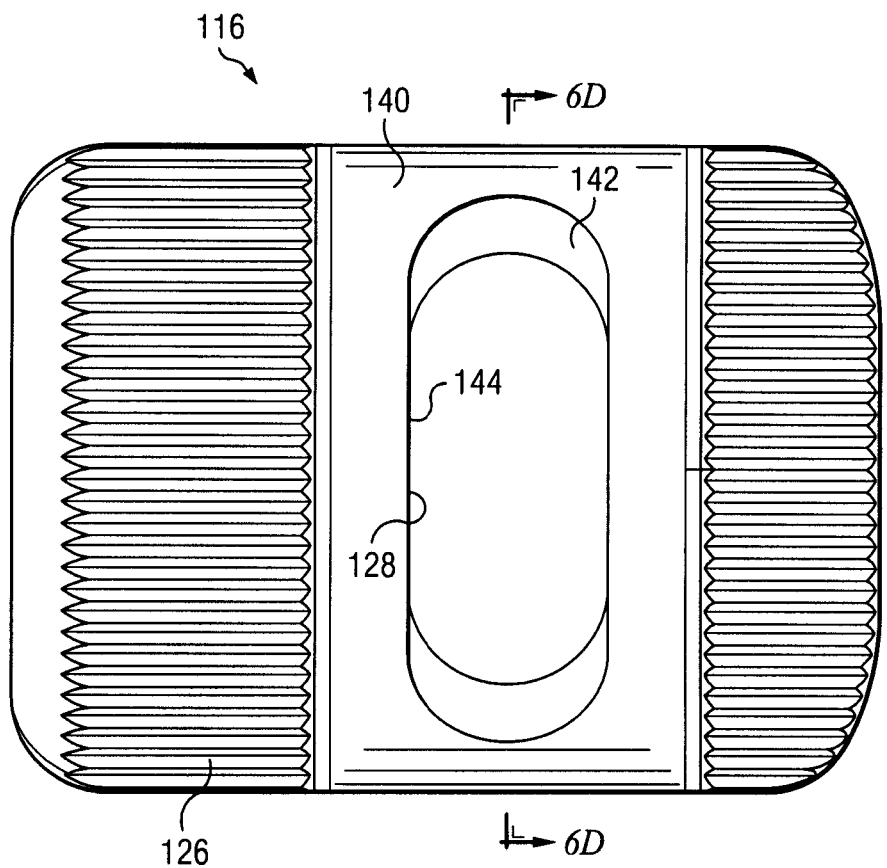
Figure 6D:
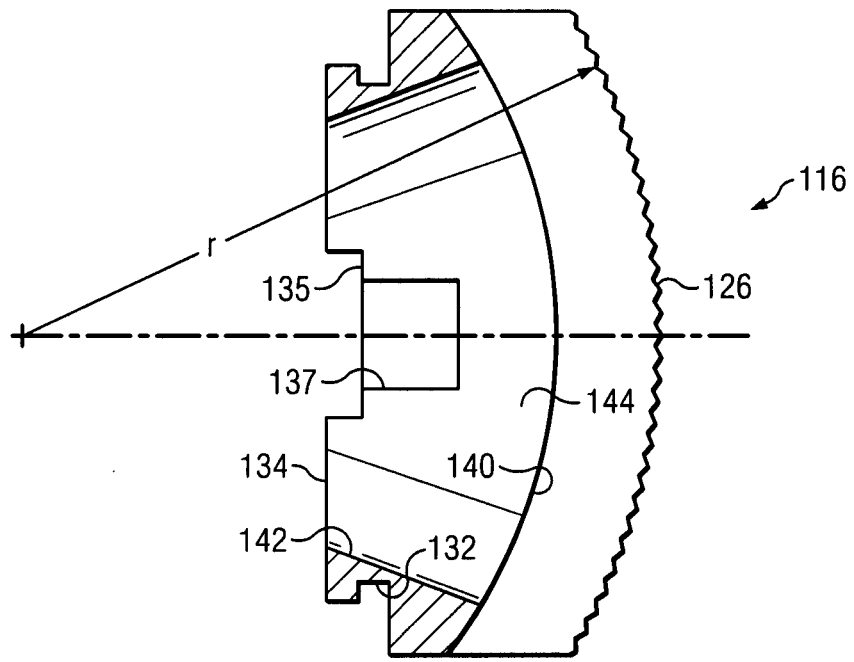

The outer clamp face 126 is a semi-cylindrical shaped surface that includes parallel, longitudinal splines shown in FIGS. 6B-6D. These are configured to interdigitate with the corresponding splines on the saddle assembly 106, as shown in FIGS. 2-4. The cylindrical shaped surface defines a radius r about which the inner jaw 116 pivots to provide the range of motion. Naturally, pivoting only occurs when the inner jaw 116 and the saddle assembly 106 are spaced so that the splines are not engaged. In some examples, in place of the splines, the inner jaw 116 includes knurling, a roughened surface, or other friction inducing features are used to enable the inner jaw 116 and the saddle assembly to be selectively secured relative to each other.

The saddle receiving area 130 is a gap formed into the outer clamp face 126. It includes a recessed articulating surface 140 that is semi-cylindrical and concentric with the outer clamp face 126. The area 130 is shaped to receive a portion of the saddle assembly 106, and the articulating surface 140 engages and articulates with the saddle assembly 106. As such, unlike the outer clamp face 126, the articulating surface 140 is configured to provide smooth rotation about the axis.

This ultimately changes the pitch of the inner jaw 116 relative to the saddle assembly 106. In the embodiment shown, the inner jaw 116 pivots relative to the saddle base 20 degrees in each direction, giving a pivot range of 40 degrees. However, it should be apparent that in other embodiments, the range of pivot articulation may be greater or less than 40 degrees, and may be affected by the diameter of the stud 108, the length of the central bore 128, as well as the angle of the bore ends 142.

The latch races 132 extend on lateral sides of the inner jaw 116. They act as sliding grooves that receive corresponding slide elements on the latch 120. The latch races 132 extend from the rearward side of the inner jaw 116 and they end above the gripping surface portion 136.

FIGS. 7A-7D show the outer jaw 118 in greater detail. The outer jaw 118 includes a front end 150, a rearward end 152, a central bore 160, an inner clamp face 154, and an outer clamp face 156. The inner clamp face 154 includes a rod-receiving transverse groove 158 adjacent the front end 150. The transverse groove 158 extends from one lateral side to another and is shaped to cooperate with the inner jaw 116 to receive and secure a bar, pin or other fixation element in place between the inner and outer jaws.

Figure 7A:
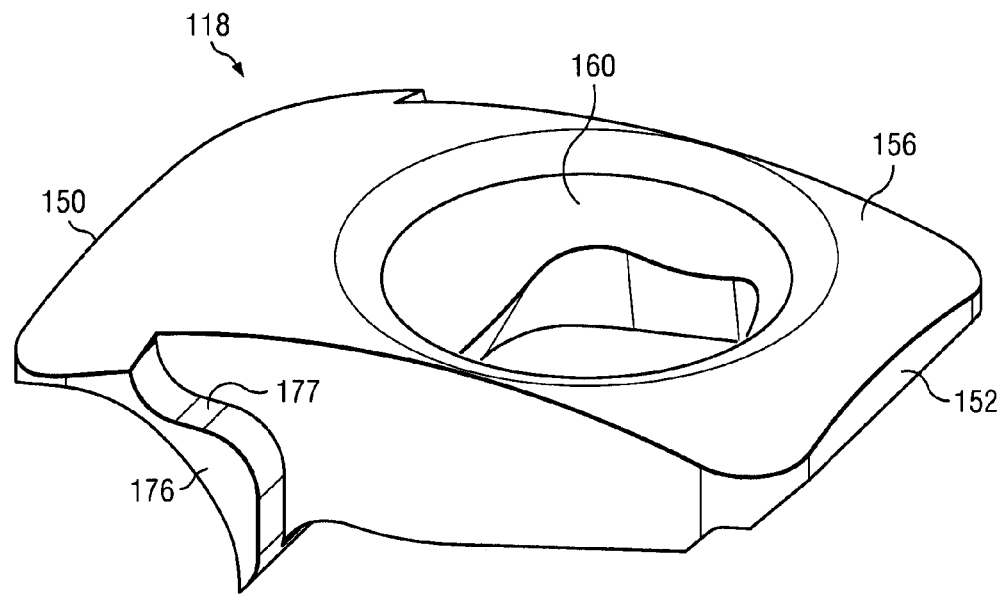
FIGS. 7A-7D are illustrations of an exemplary outer jaw of the clamping device in FIG. 2 in accordance with one exemplary aspect of the present disclosure.

As can be seen in FIG. 7A, a hook portion at the front end 150 defines a first portion of the transverse groove 158. As shown in the cross-section of FIG. 4, the groove 158 aligns with the gripping surface portion 136 on the inner jaw 116 to define a passage that captures a fixation element therein. The transverse groove 158 may be formed with a rounded bottom portion, flats, faces, or some combination of both. The central bore 160 includes features that enable it to provide articulation relative to the stud 108 in a manner that the outer jaw articulation matches that of the inner jaw 116.

In use, the outer jaw 118 displaces relative to the stud 108 in the lateral direction as the inner jaw 116 pivots with respect to the saddle assembly 106. In addition, the outer jaw 118 displaces relative to the inner jaw 116 to open the jaws to receive a fixation element between the jaws and into the transverse groove 158. This displacement is in the longitudinal direction, and as shown in FIGS. 4 and 7C, the neck 162 of the central bore 160 is shaped large enough to permit pivoting about the center of the concave curves longitudinally as well as laterally.

Figure 7B:
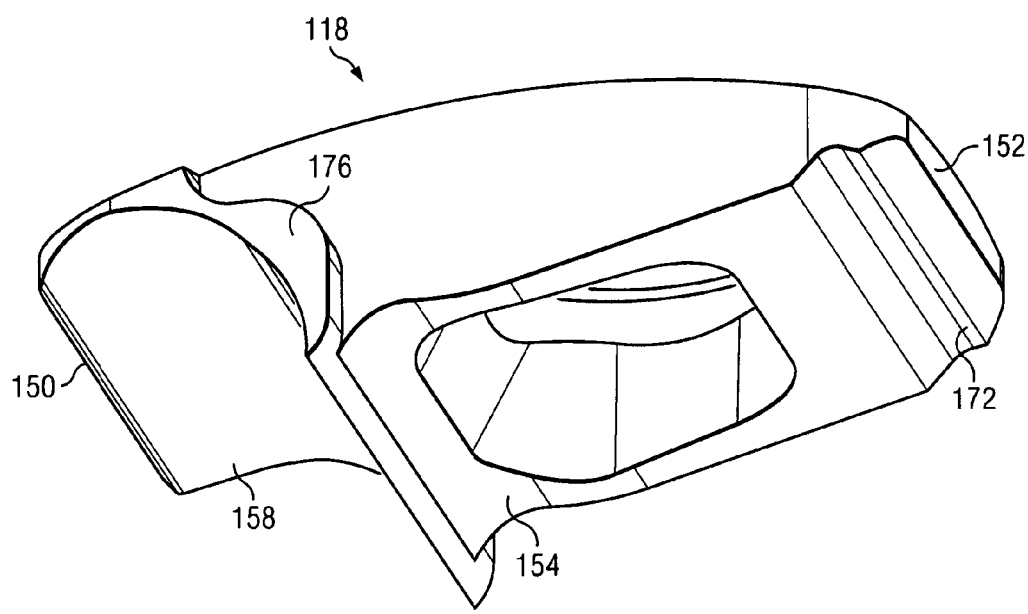
Figure 7C:
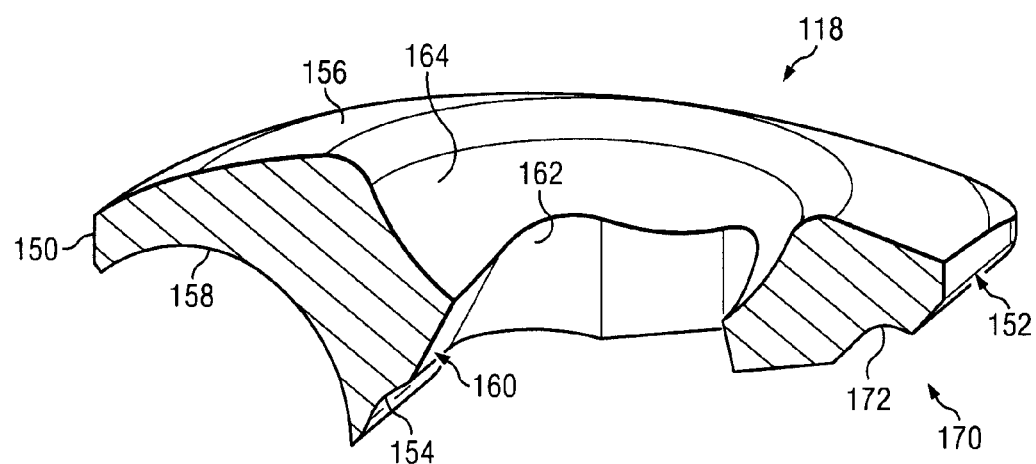
Figure 7D:
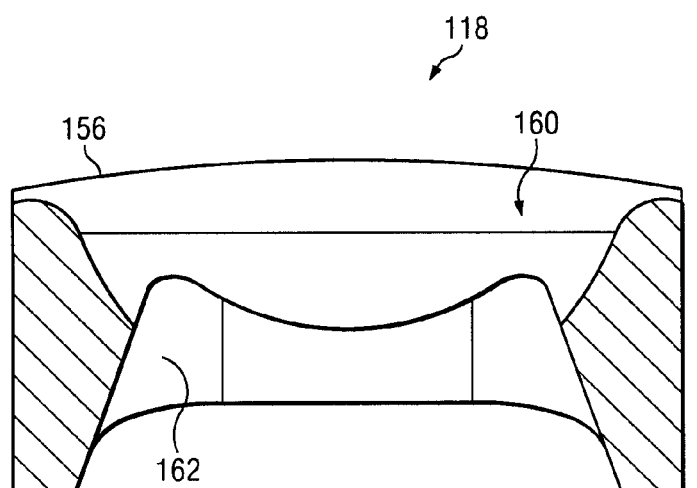

Referring now to FIGS. 7A-7C, the rearward end 152 of the outer jaw 118 includes a locking arrangement 170 shaped to contact or otherwise interface with the latch 120 to secure the outer jaw 118 in the open position, and shaped to release the outer jaw 118 so that it may pivot to capture a fixation element and secure it in the provisionally locked position. This locking arrangement 170 extends obliquely relative to the inner clamp face 154 and the outer clamp face 156 and includes a protruding engagement surface or catch surface 172 formed as a step or ridge that act as a catch for the latch 120 when the clamp 104 is in the open position. The catch surface 172 in this embodiment extends laterally across the rearward end 152 of the outer jaw 118.

The outer jaw 118 also includes lateral shoulders 176 formed thereon. The lateral shoulders are shaped and configured to contact or otherwise interface with the latch 120 to limit jaw travel and mechanically interfere with opening of the bar clamp 104 when the latch 120 is in the closed position. The lateral shoulders 176 are disposed on both lateral sides of the outer jaw 118 and are formed adjacent the groove 158. In this embodiment, the lateral shoulders 176 include an engagement surface formed as a step or ridge that acts as a catch surface 177 for the latch 120 when the latch 120 is a closed position. As will become apparent from the discussion below, the catch surface 177 is formed to cooperate with the catch surface 172 to jointly cooperate with the latch 120 to secure the outer jaw 118 in a closed position.

The lateral shoulders 176 are disposed to cooperate with the latch 120 to mechanically prevent the front end of the jaws from separating. Because of this, the mechanical interference is located on the clamping side of the stud 108. In addition, as can be seen in the example shown the catch surface 177 is, at least in part, disposed at a location longitudinally in-line above the groove 158, where the fixation element is captured. Furthermore, as will become apparent from the discussion below, the latch 120 is configured to extend above a portion of the outer jaw 118 and extend below a portion of the inner jaw 116 as a locking latch that captures at least portions of the outer and inner jaws 116, 118 therebetween to prevent or limit separation of the clamping ends of the outer and inner jaws. In this way, the jaws can be mechanically prevented from separating and releasing the pin or rod.

Figure 8A:
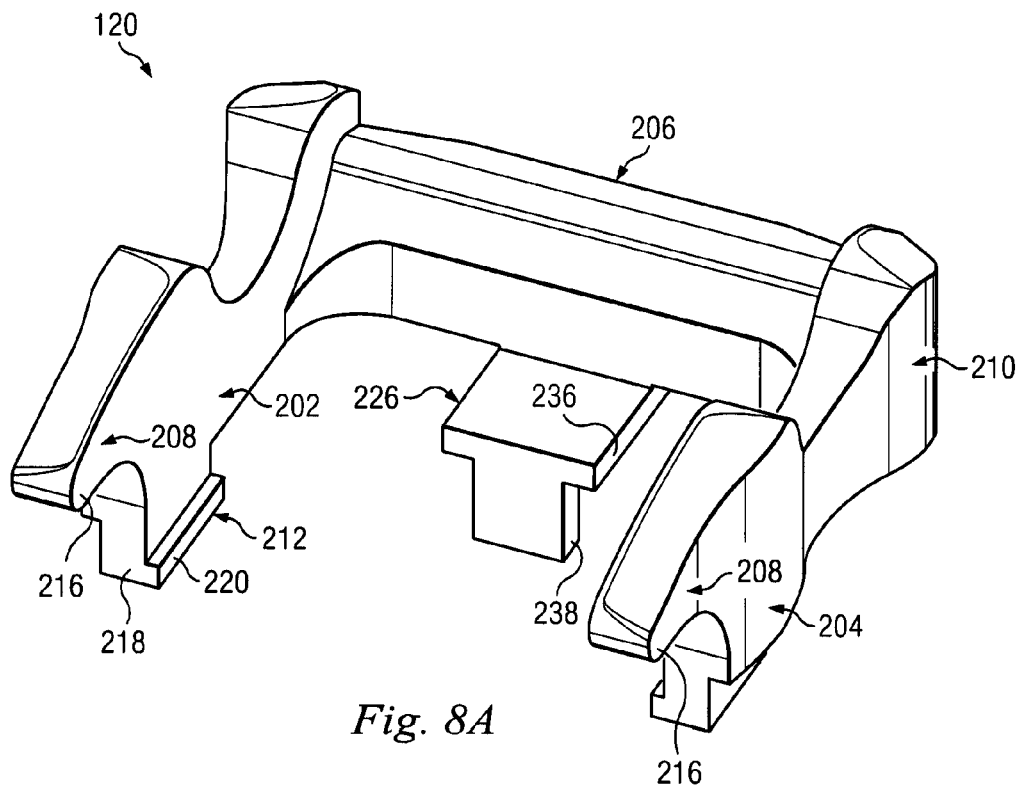
FIGS. 8A-8B are illustrations of an exemplary latch of the clamping device in FIG. 2 in accordance with one exemplary aspect of the present disclosure.
Figure 8B:
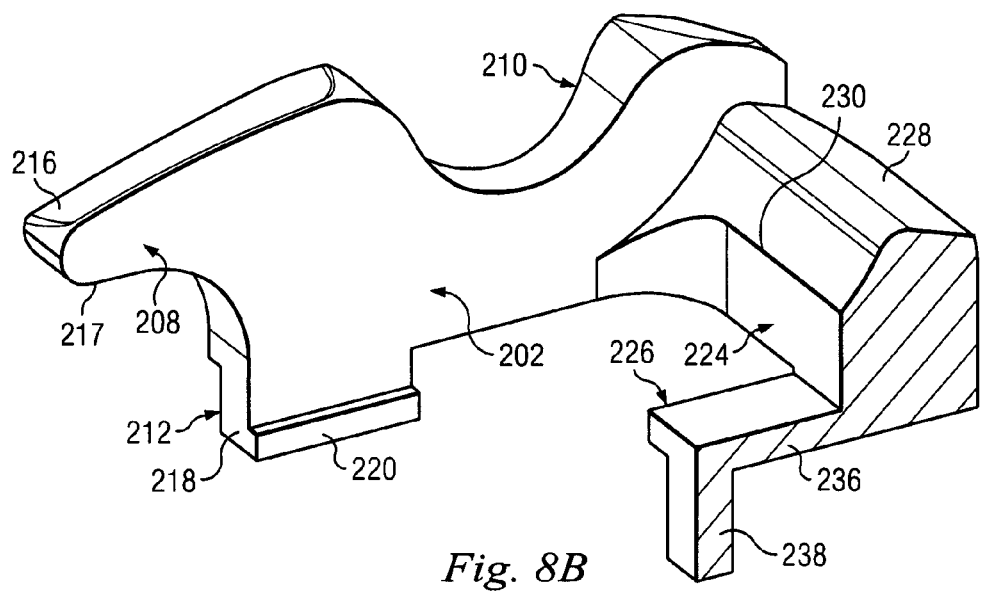

FIGS. 8A and 8B show the latch 120 in greater detail. The latch 120 is a U-shaped element arranged to interface with both the inner and outer jaws 116, 118 to lock the jaws in a provisionally locked position. The latch 120 includes first and second lateral arms 202, 204 connected by a rearwardly disposed cross bar 206.

The first and second lateral arms 202, 204 each include a forward portion 208, a rearward portion 210, and a hook portion 212. The forward portion 208 includes a forwardly projecting leading tip 216 that is located to interface with the lateral shoulders 176 of the outer jaw 118 when the latch 120 is in a locking position. In this example, the leading tip 216 is disposed at a location on the latch 120 to extend above at least a portion of the outer jaw 118. The leading tip 216 is relatively narrow, and it extends from the main body of the latch at a location an in a manner that it can extend above the rod or pin carried in the clamp assembly 104. In the example shown the leading tip 216 includes an engagement surface 217 configured to engage the outer jaw 118. In other embodiments however the projection leading tip 216 is configured to engage the fixation element itself, securing it against the inner jaw 116 and preventing removal. An edge of the latch 120 extends in a curve from the leading tip 216, extending in a substantially transverse direction, to the latch body, in a substantially longitudinal direction.

The hook portion 212 projects from a bottom of the latch 120. The hook portion 212 is shown as being substantially disposed toward the forward portion 208. However, in other embodiments, the hook portion 212 extends along the entire bottom portion of the latch 120 to the rearwardly disposed cross-bar 206. The hook portion 212 includes a base 218 and a projection 220, with the projection extending laterally inward. The hook portion 212 is located and configured to be received in and slide relative to the latch race 132 in the inner jaw 116. Accordingly, it limits the sliding motion of the latch 120 to a forward and rearward direction only.

The rearwardly disposed cross bar 206 extends between and connects the rearward portions 210 of the first and second lateral arms 202, 204. It is a rigid structure that includes a main body portion 224 and a biasing tab 226.

The main body portion 224, best seen in the cross-sectional view of FIG. 8B, includes a lock close interface 228 and a lock open interface 230. The lock-close interface 228 is shaped and configured to interface with the catch surfaces 172 on the outer jaw 118 to place the outer jaw 110 in the provisionally locked condition. As will become apparent further below, the lock-close interface 228 interfaces with the outer jaw 118 and mechanically separates the rearward ends of the inner and outer jaws 116, 118. In this example, the crossbar 206 itself acts as a wedge that is selectively disposed between the inner and outer jaws 116, 118 to limit the relative rotation of the jaws, thereby cooperatively limiting the separation distance of the jaws at the clamping side. Accordingly, the lock-close interface 228 is the surface that interfaces with the outer jaw 118 to prevent the outer jaw 118 from moving relative to the inner jaw 116 and opening the jaws. The lock open interface 230 is a surface on the main body portion 224 that engages the outer jaw 118 when the jaw is in an open condition. That is, with the latch 120 disposed rearwardly so that the cross-bar 206 is not interfering with rotation of the outer jaw 118, the lock open interface 230 rests against a rearward surface of the outer jaw 118. As such, the lock open interface 230 may cooperate with the rearward end 152 of the outer jaw 118 to permit the outer jaw 118 to rest in the opened receiving position.

The biasing tab 226 projects downwardly and is configured to cooperatively engage the inner jaw 116. It is centrally disposed on the crossbar 206, and it comprises an alignment portion 236 and a load tab 238. The alignment portion is a transversely extending portion shaped and arranged to fit within the alignment groove 135 in the inner jaw 116. As such, it has a width that permits smooth translational movement within the alignment groove 135, while providing structural support. It is disposed below the main body portion 224 so that as the cross bar 206 translates along the body surface portion 134 of the inner clamp face 124, the alignment portion 236 travels within the alignment groove 135. It has a first end that extends from the main body portion 224 toward the clamping end of the clamp 100 and it has a second end that ends substantially flush with a rearward surface of the crossbar 206.

The load tab 238 extends at a right angle from the alignment portion 236 and is configured to extend into the biasing channel 137 in the alignment groove 135. As such, it has a width less than the width of the alignment portion 236. The load tab 238 has a biasing surface thereon that interfaces with a biasing element 133 shown in the cross-sectional view of FIG. 4. Additional details and operation of the clamp can be understood by referring to U.S. patent application Ser. No. 13/175,343 filed Jul. 1, 2011, incorporated by reference herein in its entirety.

Figure 9A:
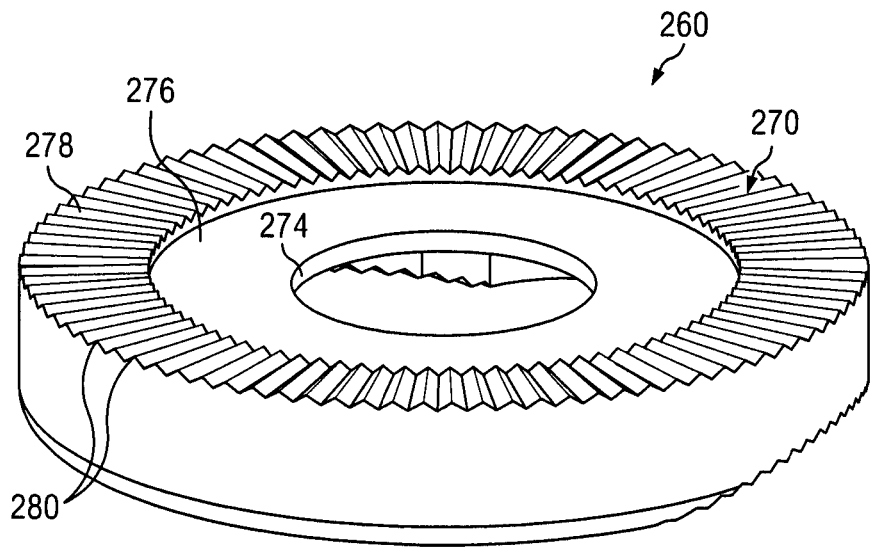
FIGS. 9A-9B are illustrations of an exemplary saddle of the clamping device in FIG. 2 in accordance with one exemplary aspect of the present disclosure.
Figure 9B:
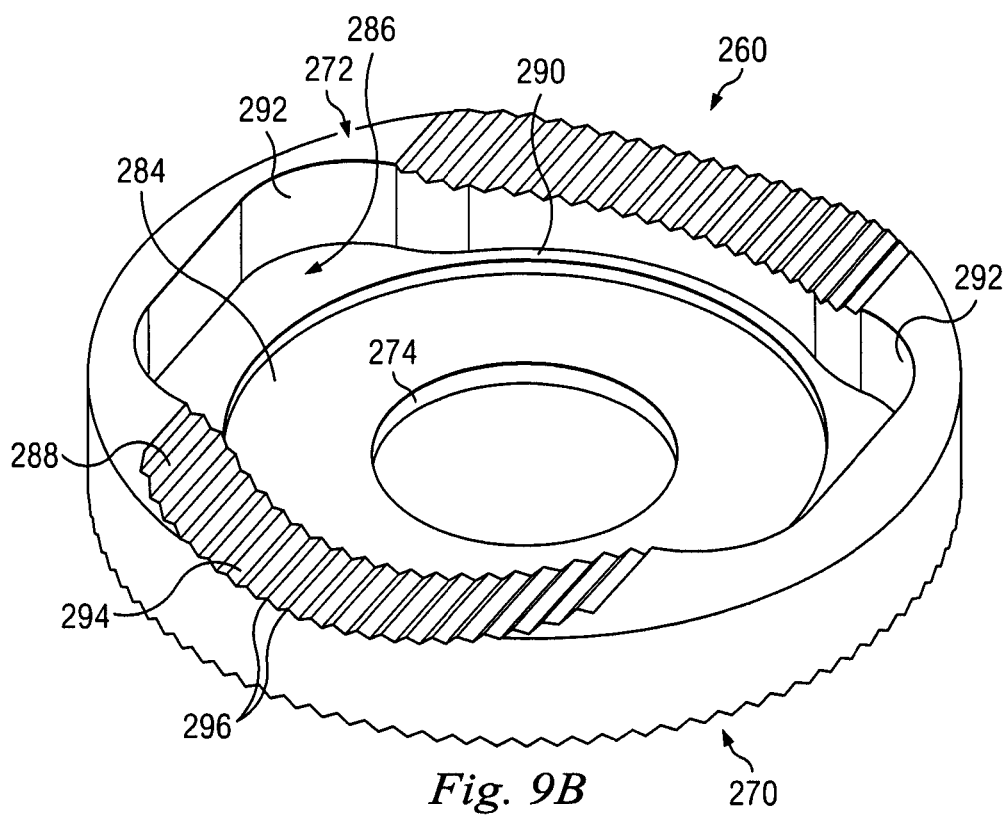
Figure 10:
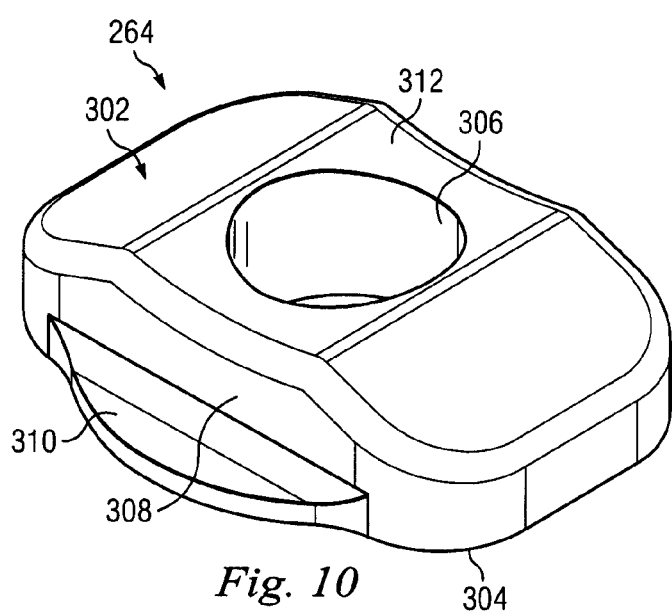
FIG. 10 is an illustration of an exemplary spacer of the clamping device of FIG. 2 in accordance with one exemplary aspect of the present disclosure.

FIGS. 9-10 show components of the exemplary saddle assembly 106. The saddle assembly 106 is arranged to permit the bar clamp 102 to rotate relative to the pin clamp 104 when the clamping device 100 is in an unlocked or in a provisionally locked condition. In addition, the saddle assembly 106 provides a foundation or base for each of the bar clamps 102 to independently pivot about the pitch axis 130 in FIG. 2 relative to the pin clamp 104. FIG. 4 shows a cross-section of the saddle assembly 106a disposed about the stud 108. The saddle assembly 106 includes a saddle 260a and a spacer 264a.

Biasing elements, such as spring washers 268a-b, separate the saddle 206 and the spacer 264. FIGS. 9A and 9B show an exemplary saddle 260 and FIG. 10 shows the exemplary thru spacer 264. The first and second saddles 260a, 260b are, in this embodiment, identical to each other and are both represented by the exemplary saddle 260 in FIGS. 9A and 9B.

Referring to these figures, the saddle 260 includes an inner facing side 270 and an outer facing side 272. FIGS. 3 and 4 show the inner facing side of the saddle 260a facing the pin clamp 104, while the outer facing side 272 is arranged to face the adjacent inner jaw of the bar clamp 102a. The inner facing side is shown in FIG. 9A and the outer facing side is shown in FIG. 9B. Starting with the inner facing side 270, the saddle 260 includes a centrally disposed through hole 274, a bias member or spring washer seat 276, and a pin clamp interfacing portion 278 with radial interdigitations 280. The through hole 274 is a central bore extending from the inner facing side 270 to the outer facing side 272. It is sized and configured to receive the stud 108 and is sized to permit the saddle 260 to freely rotate about the stud 108. The spring washer seat 276 and the pin clamp interfacing portion 278 are concentrically disposed about the through hole 274. As shown in FIG. 9A, the spring washer seat 276 is an indentation sized to receive a portion of the spring washer 268 when the spring washer 268 is in a compressed condition. The pin clamp interfacing portion 278 is disposed between the spring washer seat 276 and the saddle perimeter and is configured to selectively engage with and provide positive retention from planar rotation when the saddle and pin clamp are clamped together, thereby preventing relative rotation between the saddles 260 and the pin clamp when the clamping device 100 is in a fully locked condition. In this example, the pin clamp interfacing portion 278 includes the radial interdigitations or splines that engage corresponding radial interdigitations on the pin clamp 104 (described below) when the clamping device 100 is fully locked. It is worth noting that the spring washer 268a is disposed between the saddle 260 and the pin clamp 104. When the clamping device 100 is an unlocked or provisionally locked condition, the saddle 260 and the pin clamp are biased apart by the spring washer 268a. As such, the saddles 260 and the pin clamp 104 can rotate relative to each other. However, when placed in a locked condition, the spring washer 268a compresses within the spring washer seat 276 and the opposing radial interdigitations engage, preventing further relative rotation.

The outer facing side 272 includes a bias member seat or spring washer seat 284, a spacer seat 286 configured to receive the thru spacer 264, and a clamp interfacing portion 288.

The spring washer seat 284 is concentrically disposed about the through hole 274. As shown in FIG. 9B, the spring washer seat 284 is an indentation sized to receive a portion of a spring washer 268 when the spring washer 268 is in a compressed condition. The spacer seat 286 is a non-circular shaped recess that prevents relative rotation between the saddle 260 and the corresponding spacer in the spacer seat 286. In this example the spacer seat 286 includes a main portion 290 and two peripheral wings 292 that extend from the main portion 290. As will become apparent further below, a spring washer in the spacer seat 286 biases the spacer in the spacer seat 286 to an offset or displaced condition when the clamp 100 is in an unlocked or provisionally locked condition.

The clamp interfacing portion 288 is disposed between the spacer seat 286 and the saddle perimeter and is configured to selectively engage with and prevent relative pivoting between the saddle 260 and the pin clamp 104 when the clamping device 100 is in a fully locked condition. As such, the clamp interfacing portion 288 includes a concave saddle portion 294 having about or substantially the same radius as the cylindrical portion of the inner jaw 116. In this example, the concave saddle portion 294 includes linear splines 296 that are shaped to engage corresponding linear splines on the inner jaw 116 of the bar clamp 102 when the clamping device 100 is in a fully locked condition. It is understood that the saddle 260b corresponds to and interfaces with the bar clamp 102b.

The thru spacer 264 is shown in FIG. 10. It includes a clamp facing side 302 and a saddle facing side 304. The saddle facing side 304 in FIG. 4 is disposed within the spacer seat 286 and interfaces with the spring washer 268a, while the clamp facing side 302 is arranged to face the adjacent inner jaw 116 of the pin clamp 104. The saddle facing side 304 includes a boss, as can be seen in FIG. 4, and includes a through hole 306 that extends from the saddle facing side 302 through the jaw facing side 304. The through hole 306 is sized and shaped to permit the thru spacer 264 to rotate with its corresponding saddle 260 about the stud 108. The clamp facing side 302 includes a main body 308 and flanges 310 extending on opposing sides of the main body 308. The flanges 310 are shaped and configured to sit within the spring seat 286 to cover the spring washer, while the body fits into the wings of the spacer seat 292 to prevent relative rotation between the thru spacer 264 and the saddle 260. The main body 308 includes a height substantially greater than the flanges 310 that projects out from and above the spacer seat 286. The top of the main body 308 includes a smooth cylindrical surface 312. In use, the smooth cylindrical surface 312 concentrically mates with the cylindrical articulating surface 140 of the inner jaw 116. The height of the main body 308 is selected to cooperate with the depth of the saddle assembly receiving area 130 in the outer clamp face 126 to selectively engage and disengage the linear splines of the saddle 260 with the linear splines on the outer clamp face 126 of the inner jaw 116. Particularly, when the spring washer 268 is in an uncompressed state, the thru spacer 264 is offset from the saddle 206. This offset correspondingly offsets the inner jaw 116 from the saddle 260 so that the linear splines of the saddle 260 and the inner jaw 116 are disengaged. In this condition, the inner jaw 116, and thus the entire pin clamp 104, may pivot about the pitch axis 30 relative to the saddle assembly 106, with the cylindrical articulating surface 140 of the inner jaw 116 interfacing with the cylindrical surface 312 on the main body 308 of the thru spacer 264. When the clamp system 100 is placed in the fully locked condition, the spring washer 268 compresses, the offset is reduced or eliminated, and the thru spacer 264 seats more completely or fully within the spacer seat 286. Likewise, the inner jaw 116 moves closer to the saddle 206 until the linear splines on the cylindrical surface of the inner jaw 116 engage the linear splines 296 on the cylindrical concave saddle portion 294 of the saddle 206. This locks the clamp 104 to the saddle assembly 106, preventing further pivoting rotation about the axis.

Figure 11A:
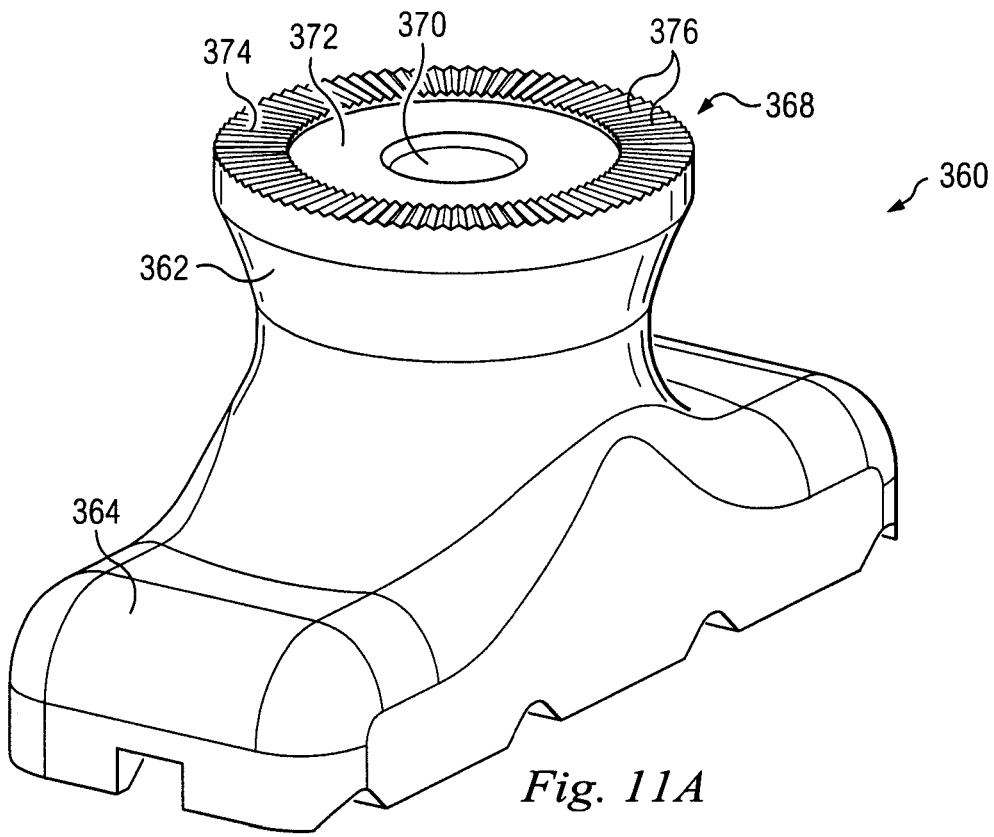
FIGS. 11A-11B are illustrations of an exemplary pin jaw of the clamping device of FIG. 2 in accordance with one exemplary aspect of the present disclosure.
Figure 11B:
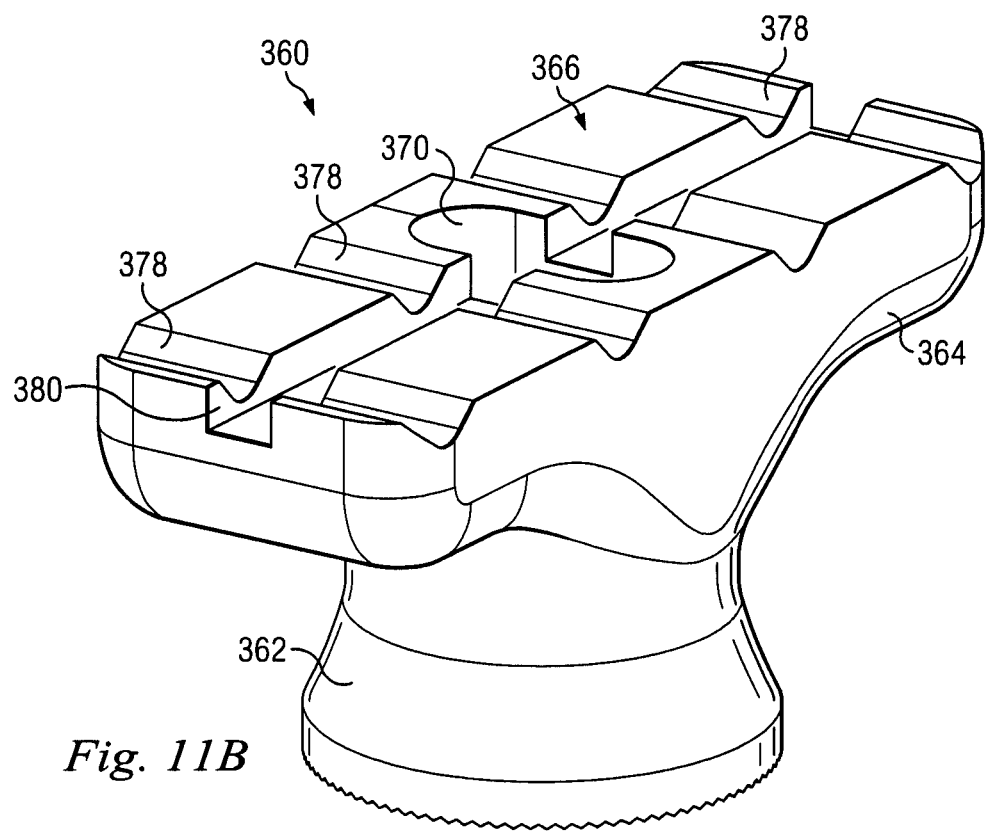

FIGS. 11A and 11B show the components making up the pin clamp 104. In this example, the pin clamp 104 comprises two identical jaws, referenced herein by the numeral 360. The pin jaw 360 comprises a neck 362, a body 364, an inner clamp face 366, and an outer clamp surface 368. The neck 362 is arranged with a substantially round cross-section that leads to the outer clamp surface 368. As shown in FIG. 11A, the outer clamp surface 368 comprises a centrally disposed through hole 370, a bias member or spring washer seat 372, and a saddle interfacing portion 374 with radial interdigitations 376. Interdigitations are not limited to poker-chip serrations, but also include any series of features that interfere to restrict relative rotation. The spring washer seat 372 and the saddle interfacing portion 374 are concentrically disposed about the through hole 274. As shown in FIG. 11A, the spring washer seat 372 is an indentation sized to receive a portion of the spring washer 268a when the spring washer 268a is in a compressed condition. The saddle interfacing portion 374 is disposed between the spring washer seat 372 and the surface perimeter and is configured to selectively engage with and provide positive retention from planar rotation when the outer clamp surface 368 is clamped to the saddle 260, thereby preventing relative rotation between the saddle 260 and the pin clamp 104 when the clamping device 100 is in a fully locked condition. In this example, the saddle interfacing portion 374 includes the radial interdigitations or splines that engage corresponding radial interdigitations on the saddle 260 when the clamping device 100 is fully locked. The through hole 370 is a central bore extending from the outer clamp surface to the inner clamp 366. It is sized and configured to receive the stud 108. The through hole 370 is shown in cross-section in FIGS. 4 and 5, and its profile changes from the round hole opening in the outer clamp surface 368 shown in FIG. 11A to the more rectangular opening in the inner clamp face 366 shown in FIG. 11B. This change in profile cooperates with corresponding features on the stud 108 to prevent rotation of one pin jaw 360 relative to the other, maintaining alignment of the pin jaws.

The inner clamp face 366 shown in FIG. 11B is a substantially flat surface that creates a plane substantially parallel to a plane created by the outer clamp surface 368. The inner clamp face 366 creates the multi-pin clamp by including a plurality of grooves 378 that each can receive a separate pin 14 as shown in FIG. 1. In this example, the inner clamp face 366 includes four grooves 378. However, other embodiments include pin jaws having two grooves, six grooves, and in some embodiments, eight grooves. Other numbers of grooves are contemplated, including embodiments with odd numbers of grooves. In this embodiment, each groove 378 is formed having V-shaped sides, connected by a rounded portion having a radius. In this example, a central notch 380 is formed in the inner clamp face 366. This central notch 380 is configured to cooperate with a tissue protector as described further below to secure the tissue protector and provide additional stability during surgical procedures.

Figure 12:
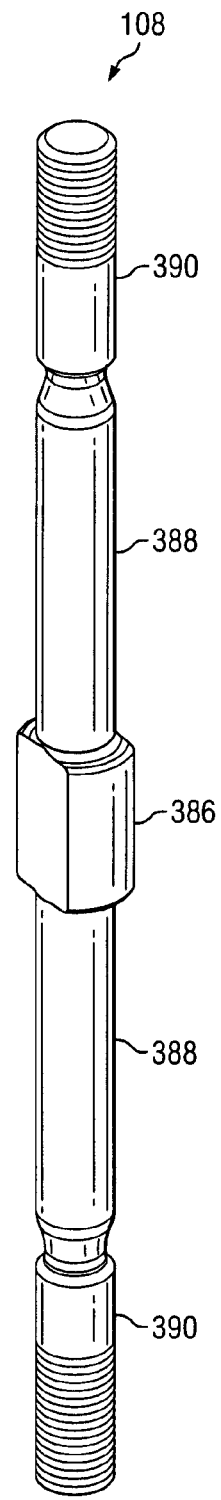
FIG. 12 is an illustration of an exemplary stud of the clamping device of FIG. 2 in accordance with one exemplary aspect of the present disclosure.

FIG. 12 shows the stud 108 in greater detail. The stud 108 includes a substantially rectangular cross-section in a middle section 386 that corresponds with a matching shape in the through hole 370 in the pin jaw 360. It also includes cylindrical portions 388 away from the middle section 386 that permits the rod clamps 102 on either end of the pin clamp 104 to rotate about the stud 108, along with the respective saddle assemblies 106. Although a rectangular cross-section is shown, other embodiments include alternative non-circular cross-sections that correspond to or otherwise mate with the cross-section of the hole 370 to prevent relative rotation between the rod and the pin clamp jaws 360. Threaded ends 390 cooperate with the nuts 112 to allow the nuts to be tightened onto the clamping device 100 or to loosen the clamping device 100. As can be seen, the stud 108 is free to slide axially for a distance in either direction relative to the pin jaws and the rod clamps, so that when one of the nuts 112 is tightened, the other nut 112 is drawn in reducing the distance between the nuts and clamping the pin clamp 104 and both rod clamps 102.

To explain in greater detail, the two pin jaws 360 of the pin clamp 104 will typically be placed onto two bone-engaging external fixation elements that will fit into the grooves 378 in the inner clamp faces 366 as shown in FIG. 1. Next, each of the rod clamps 102 can be clamped onto external fixation elements, such as rods or bars, tying them into the external fixation system. The stud 108 provides a central axis of rotation so that the clamps 102a, 102b, 104 can all be rotated in a different angular position relative to each other about the yaw axis 40 in FIG. 2. To allow greater flexibility, each of the two outer rod clamps interface with a saddle assembly 106 and the bottom jaw 116 is configured to selectively rotate about the pitch axis 30 transverse to the yaw axis 40. In addition, the external fixation elements (shown as bar or rods 12 in FIG. 1) gripped by the rod clamps 102 have their own roll axes 20, and the entire clamping device 100 can rotate about these axes.

Once all external fixation elements are assembled into the respective jaws and aligned in the proper orientation, one of the two nuts 112 can be tightened. This draws all of the components together, compressing the bar clamps 102 and the pin clamp 104, thereby capturing the external fixation elements and holding everything in place. Because the stud 108 is restricted from rotating relative to the pin jaws 360, but free to slide longitudinally for a distance relative to all the clamps, as the nut 112 is tightened on the stud 108, the distance between the nuts decreases. Either nut 112 can be tightened to achieve the same result.

In some embodiments, instead of both pin jaws 360 being restricted from rotation relative to the stud 108, only one of the pin jaws 360 is restricted from relative rotation. In other alternatives, one of the elements of one of the rod clamps 102, or even a separate element that can be held by the user restricts rotation of the stud 108. In this particular embodiment, the pin clamps 360 are used to prevent rotation of the stud during tightening because they are larger and because this keeps them oriented to each other prior to having the external fixation elements inserted in the jaws.

In an alternative embodiment, the clamping device includes the multi-pin clamp 104 and only one other clamp. It is worth noting that more than three clamps could be incorporated into one clamping device if there was a need.

FIGS. 13-19 show an alternative embodiment of a clamping device 500 usable in the external fixation system 10 of the present disclosure. Much of the discussion relating to the clamping device 100 discussed above is relevant to the embodiment shown in FIGS. 13-19 and, in an effort to avoid duplicity and for ease of understanding, will not be replicated in its entirety.

Figure 13:
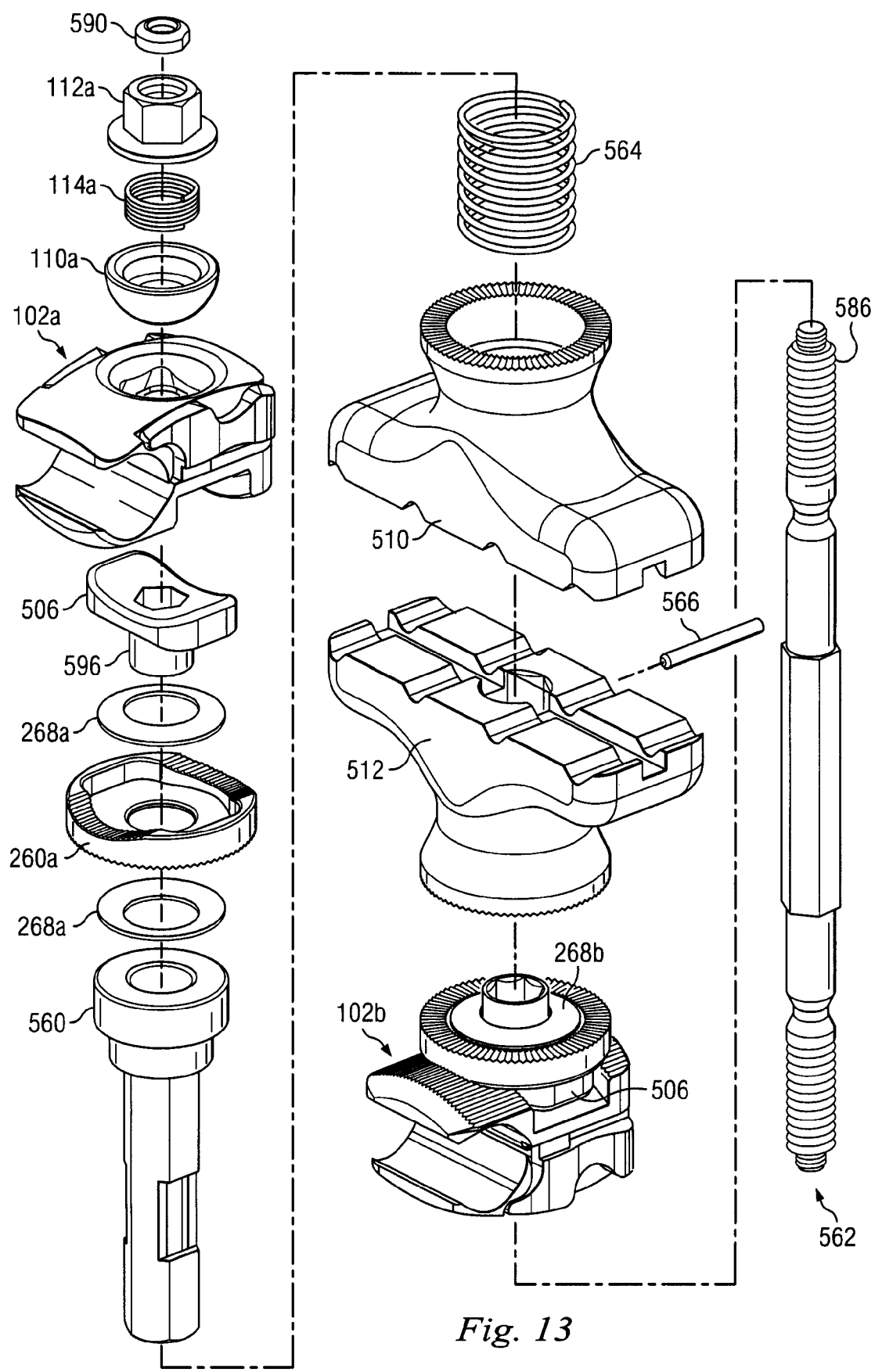
FIG. 13 is an illustration of a partial exploded view of an alternative embodiment of a clamping device according to one exemplary aspect of the present disclosure.
Figure 14:
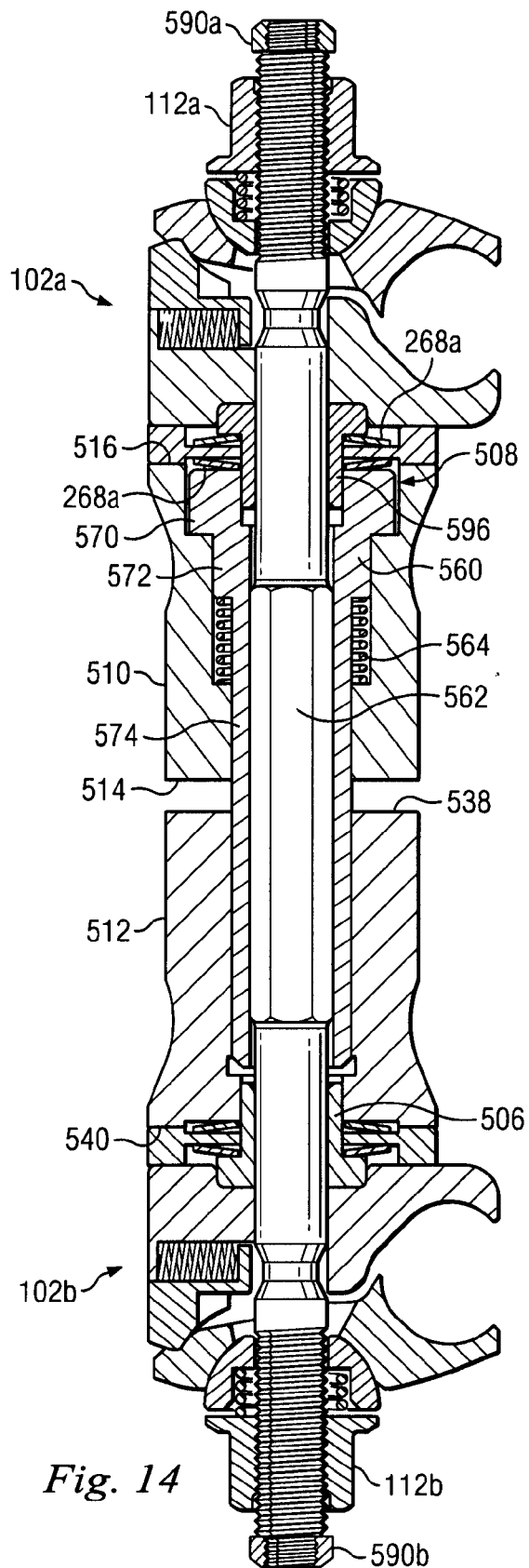
FIG. 14 is an illustration of a cross-sectional view of the clamping device of FIG. 13.
Figure 15:
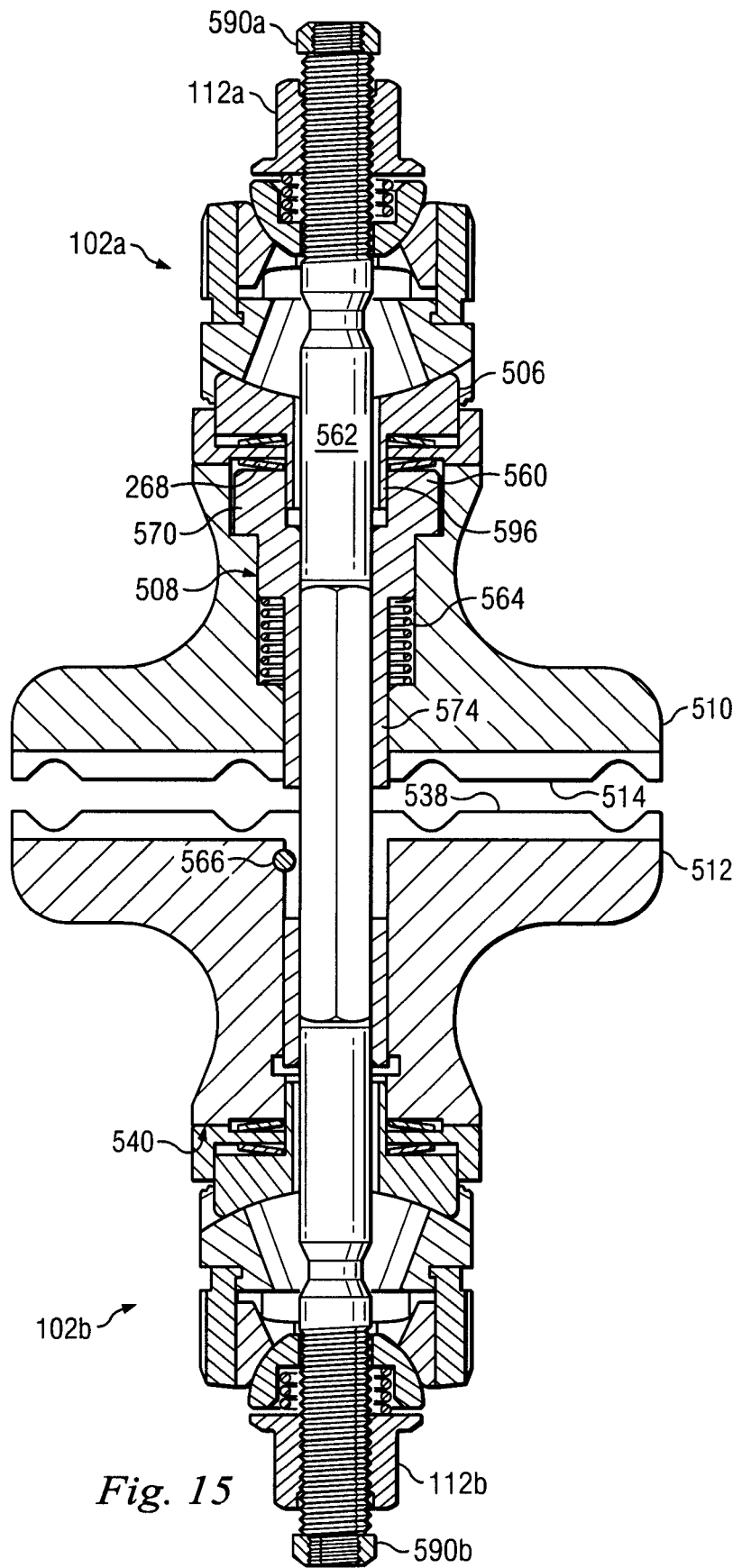
FIG. 15 is an illustration of a cross-sectional view of the clamping device of FIG. 14 taken transverse to the cross-sectional view in FIG. 14.

FIG. 13 is a partially exploded view and FIGS. 14 and 15 are cross-sectional views. Like the embodiment discussed above, the clamping device 500 includes the bar clamps 102, saddles 260, and spring washers 268. However, the clamping device 500 also includes a pin clamp 504, a spacer 506 making up a part of the saddle assembly, and a post assembly 508. The post assembly 508, in this example, includes a fixation post 560, a stud 562, a biasing element shown as a post spring 564, and a pin 566.

The pin clamp 504 in this example includes a first jaw 510 and a second jaw 512 that together cooperate to clamp or secure the bone fixation elements, such as bone pins, screws, or other fixation elements attachable to a bone segment. FIG. 16 shows another cross-section of the first jaw 510 independent of other components of the clamping device 500. The first jaw 510 includes many of the features of the pin jaws 360 discussed above, including, for example, inner and outer clamp surfaces 514, 516, a saddle interfacing portion 520, pin-receiving grooves 522, and a notch 524. Since these features were described above, they will not be re-discussed here in an effort to avoid duplicity.

In this embodiment the first jaw 510 includes a through hole 526 extending between its inner and outer clamp surfaces 514, 516. As can be seen in FIG. 16, the hole 526 includes a first region 528, a second region 530, and a third region 532. The diameter of the first region 528 is greater than the diameter of the second region 530, and the diameter of the second region 530 is greater than the diameter of the third region 532. As can be seen herein, the first and second regions 528, 530 are formed of cylindrical surfaces, while the third region 532 has a non-circular surface, shown here as a hex surface. As will be explained below, the third region 532 is formed to interface with and prevent rotation about the yaw axis relative to the post assembly 508.

The second jaw 512 is shown in cross-section in FIG. 17. The second jaw 512 includes many of the features of the pin jaws 360 discussed above, including, for example, inner and outer clamp surfaces 538, 540, a saddle interfacing portion 542, a spring washer seat 544, grooves 546, and a notch 548. Since these features were described above, they will not be re-discussed here in an effort to avoid duplicity. The second jaw 512 includes a through hole 550 extending between its inner and outer clamp surfaces 538, 540. As can be seen in FIG. 17, the hole 526 includes a first region 552 and a second region 554, with the first region 552 having a larger diameter and having a non-circular surface, shown here as a hex surface, and the second region 554 having a smaller diameter and having a cylindrical surface. In addition, the second jaw 512 includes a transverse hole 556 that intersects the though hole 550. As will be discussed further below, the transverse hole 556 is sized to receive a pin that prevents removal of the first and second jaws 510, 512 from elements of the post assembly 508.

The post assembly 508 cooperates with the rod clamps 102 and the pin clamp 504 to enable clamping of all three clamps at the same time, with a single input. In addition, the post assembly 508 is arranged to provide the pin clamp 504 with a biasing force to provisionally secure fixation elements, such as bone pins within the pin clamp 504. That is, upon insertion of bone pins into the pin clamp 504, the post assembly 508 provides a biasing clamping force that may provisionally hold the pins in place until the clamping device 500 is arranged as desired and tightened down. Accordingly, the pin clamp 504 will be less likely to fall off the bone pins before tightening, increasing ease of use and surgeon satisfaction.

Figure 18A:
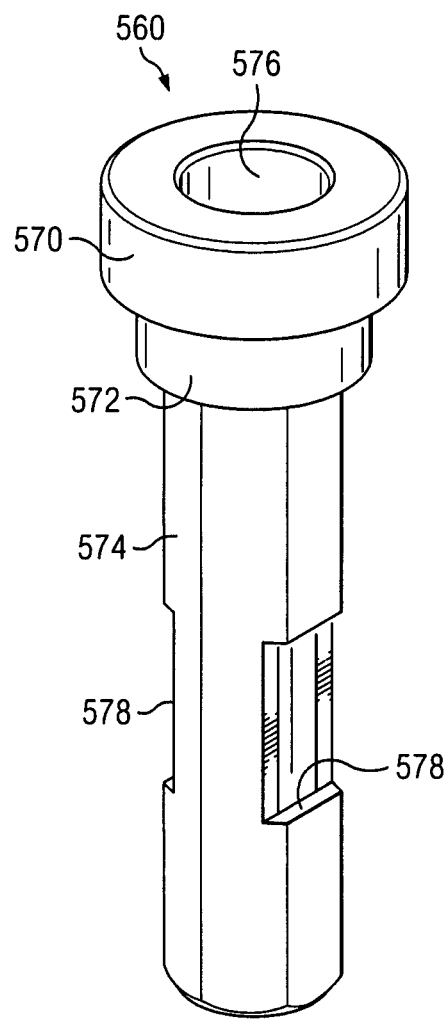
FIGS. 18A-18B are illustrations of an exemplary fixation post of the clamping device in FIG. 13 in accordance with one exemplary aspect of the present disclosure.
Figure 18B:
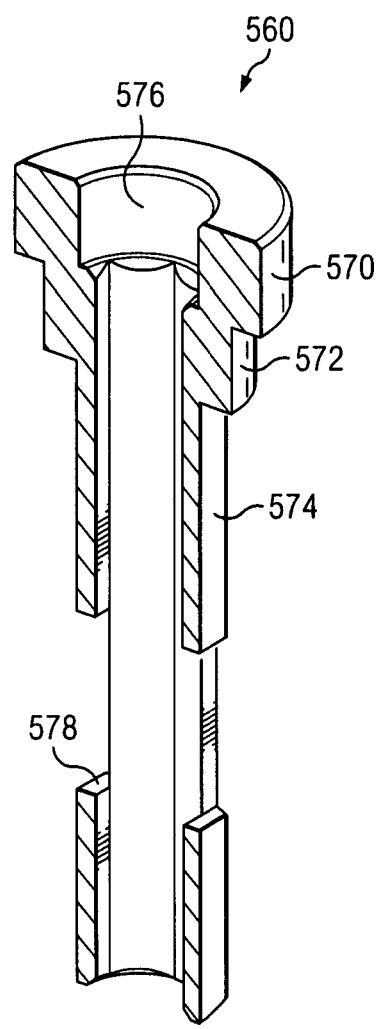

Referring to FIGS. 13-15, the post assembly 508 includes a fixation post 560, a stud 562, a biasing element shown as a post spring 564, and a pin 566. The fixation post 560 is disposed within the holes 526, 550 in the first and second jaws 510, 512. FIGS. 18A and 18B show the fixation post 560 in greater detail. The fixation post 560 includes a head portion 570, a shoulder portion 572, a body portion 574, and a through hole 576 extending through its longitudinal length. The body portion 574 is formed with a non-circular shape which, in this embodiment, is a hexagonal shape that corresponds to the non-circular shape in the holes 526, 550 in the first and second jaws 510, 512 of the pin clamp 504. Because of this corresponding non-circular shape, the first and second jaws 510, 512 are rotationally fixed with respect to the fixation post 560. The body portion 574 also includes a relief or notch portion 578 along a portion of its length. The notch 578 permits limited axial movement of the fixation post 560 relative to the first and second jaws 510, 512, as will be described further below. In this example, two notches 578 are formed on opposing sides of the body portion 574, although in some examples, a single notch is sufficient to provide the advantages. More than one notch on opposing sides of the body portion 574 however, may simplify and speed the clamping device assembly process. In this example, the notches 578 are formed as cut-outs on opposing sides of the body portion 574 and intersect with the through hole 576.

FIG. 18B shows a cross-sectional view of the fixation post 560 and shows the non-circular configuration of the through hole 576. In this example, the through hole 576 in the head portion 570 includes first and second portions, where the first portion has a circular diameter. As will be understood further below, this receives and allows the saddle spacer to rotate relative to the fixation post 560. However, the second portion has a non-circular diameter. This receives and prevents the stud 562 from rotating relative to the fixation post 560.

As can be seen with reference to FIGS. 14 and 15, the head portion 570 is sized to substantially correspond with the first region 528 of the pin clamp's first jaw 510, the shoulder portion 572 is sized to substantially correspond with the second region 530 of the first jaw 510, and as indicated above, the body portion 574 is sized to substantially correspond with the third region 532 of the first jaw 510. In addition, the body portion 574 is sized to correspond with the first region 552 of the second jaw 512. As such, the first region of the second jaw 512 is substantially equal in cross-sectional size and configuration to the third region of the first jaw 510. While they are sized to substantially correspond, they are provided with a sliding fit, as the first and second jaws 510, 512 axially displace relative to the fixation post 560. The fixation post 560 includes a first end acting as a spring washer seat 580. It is arranged so that when the fixation post 560 is disposed within the first and second jaws 510, 512 the spring washer seat interfaces with the spring washer 268.

As shown in FIGS. 14 and 15, the post spring 564 is disposed in the second region 530 of the hole 526 in the first jaw 510 around a portion of the body portion 574 of the fixation post 560. The post spring 564 is arranged to provide a biasing tension load that pushes against the shoulder portion 572 of the fixation post 560 to push the first jaw 510 of the pin clamp 504 toward the second jaw 512, thereby biasing the clamp 504 toward a closed or clamped condition. In one embodiment, the post spring 564 is sized to be substantially uncompressed when the inner clamp faces 514, 538 of the first an second pin jaws 510, 512 are substantially adjacent each other or in contact with each other, but also is sized to provide a biasing load that frictionally holds the bone pin 14 in place between the jaws when the jaws 510, 512 are separated by the bone pin 14, and before the overall clamping device 500 is tightened to lock the bone pins 14 in place. Accordingly, the post spring 564 is arranged and selected to provide a provisionally locking load on a bone pin (or other elements) disposed between the pin jaws 510, 512.

The stud 562 is shown in FIG. 13. The central region of the stud 562 has a non-circular shape that mates with the noncircular shape of the through hole 576 of the fixation post 560. In this example the non-circular shape is a hexagonal shape. Accordingly the fixation post 560 and the pin clamp 504 are rotationally fixed relative to the stud 562. The stud 562 includes end regions having a circular cross-section that extends through the respective rod clamps 102 and allows the rod clamps to rotationally pivot about the stud 562 and about the yaw axis. Threaded ends 586 receive clamping nuts 112 at each end. In this example, a smaller diameter tip is reverse threaded to receive a reverse threaded locking nut 590 that prevents removal of the clamping nut 112. In other embodiments, the stud 562 includes a spherical head at one end as a pivot interface for the bar clamp 102. Accordingly, a clamping nut may be located only at a single end of the stud.

The pin 566 extends through a pin hole in the second jaw 512 of the pin clamp 504 and cooperates with the fixation post 560 to limit the axial travel of the fixation post 560 in the jaws 510, 512 of the pin clamp 506. In one embodiment, the pin 566 has a length greater than the width or diameter of the body portion 574 of the fixation post 560 so as to interface with the fixation post while also interfacing with (such as while being disposed in the pin hole) the second jaw 512. As can be seen, the pin 566 extends into the notch 578, creating a mechanical stop that prevents removal of the fixation post 560 from the second jaw 512 and limits the directional movement of the fixation post 560. In this example, the pin 566 extends in a direction tangent to the fixation post notch 578, and in this example, is aligned parallel to one of the surfaces forming the hexagonal shape of the fixation post 560. Accordingly, in this example, the pin 566 is disposed to prevent removal of the fixation post 560, and is also disposed to not prevent or limit axial movement of the stud 562 relative to the second jaw 512. This may simplify manufacturing by allowing the pin clamp 506 to be assembled, with the fixation post 562 and post spring 564, independent of other assembly steps that would require attachment to the stud 562. In other embodiments, the pin 566 is disposed to penetrate into and/or pass through the fixation post and/or into or through notches or slots in the stud 562.

The spacer 506 is shown in FIG. 13. It is similar in many ways to the through spacer 264 shown and described above and performs similar functions and has a similar size. However, it lacks the optional flanges 310, but is nonetheless sized to fit within the saddle without relative rotation about the yaw axis. In addition, a boss 596 extending from a bottom of the spacer 506 has a longer length, as it is extends not just through the saddle 260, but also into the adjacent jaws 510, 512 of the pin clamp 506, as shown in FIGS. 14 and 15. Accordingly, the inner diameter of the head portion 570 in the fixation post 560 is about equal to the inner diameter of the second region 554 of the through hole 550 in the second jaw 512, as these both receive the boss 596.

In use, the surgeon inserts the bone pins 14 between the jaws 510, 512 of the pin clamp 504 and into the grooves 522, 546 defined in the inner clamp faces 514, 538. The pins 514 may be inserted laterally or axially between the jaws. Since the post spring 564 biases the jaws 510, 512 toward each other, insertion of the bone pins 14 separates the jaws 510, 512 slightly and compresses the post spring 564. This spring force acts to maintain a load on the pins such that the pins are frictionally held in the pin clamp 504 reducing the chance of inadvertently removing or dropping the bone pins 14 from the clamp 504 or having the clamp inadvertently slip along or fall off the pins before final tightening. The surgeon may then drive the pins into the bone as desired.

Fixation rods 12 may also be introduced into the rod clamps 102 at both ends of the fixation device 500. The arrangement of the rod clamps 102 enables the rods to be provisionally clamped, where spring forces or mechanical interference prevents inadvertent removal of the rods from the rod clamps. Thus, the bone pins and the rods are provisionally held, but not firmly locked in place in the clamping device 500. With the pins and rods provisionally held, the clamping device can be manipulated to provide the desired arrangement for the fixation frame that best serves the patient. This may include adjusting the pins in the pin clamp or adjusting the rods in the rod clamps. Adjustment may include manipulation in any of the pitch, roll, and yaw axes, including axial sliding along the pins or rods.

When the clamping device 500 is arranged as desired, the surgeon locks all three clamps in the clamping device 500 against further movement by tightening a single clamping nut 112 on the stud 562. As discussed above, by virtue of the non-circular portions of the stud 562, the fixation post 560, and the jaws 510, 512 of the pin clamp 504, rotation of the pin clamp 504 relative to the stud 562 is prevented and tightening only a single clamping nut 112 can place all three clamps of the clamping device 500 in the final locked state. As the clamping nut 112 is tightened, the spring washers 268 compress. As the spring washers 268 compress, the interdigitations on the saddles and the first and second pin jaws 510, 512 provide positive retention from planar rotation about the yaw axis. In addition, the spring washers 268 separating the saddles 260a, 260b and the spacers 264 compress, and the splines on the inner jaws engage the splines on the concave side of the saddles 260a, 260b, and the spherical washers 110 respectively tighten against the outer jaws of the rod clamps 102. Thus, all three clamps are placed in a fully locked state, preventing all relative movement of the clamps and the fixation elements.

To release the fixation elements, the surgeon performs the steps in reverse. Particularly, he first loosens one of the clamping nuts 112, placing the clamping device 500 in the provisionally locked state. Then he may grasp and pull the latch 120 of the bar clamps 102 so that the cross bar 206 moves out from between the inner and outer jaws. The jaws will then separate opening the clamp, and the bar may be removed. The pins may be removed by laterally or axially removing them from between the pin jaws 510, 512.

Although shown as including two nuts, one embodiment includes only a single nut at one end of the stud 562. The other end of the stud is configured in the shape of a locking element, such as the nut or in the shape of a the spherical washer that interfaces directly with the outer jaw.

One exemplary embodiment of the disclosure provides a tissue protector that may be employed with the pin clamps described above. As described above, it can be challenging to place pins in bones that are intended to be secured in multi-pin clamps without the use of a guide or without the use of sleeves clamped by the multi-pin clamp that act as guides. However, instead of having to remove guides and replace them with clamps or instead of having to tighten clamps on the sleeves, then later loosen the clamps to remove the sleeves and retighten to clamp the pins, the pin clamps disclosed herein are made to secure a tissue protecting sleeve without the steps of tightening screws.

FIGS. 19-24 disclose a protective sleeve 800 usable with the clamping devices described above to guide placement of the pins into a patient's bone, without requiring repetitive tightening and loosening, and tightening of the clamp. Instead, the sleeves 800 are configured to secure to and cooperate with the clamp to guide placement of the pins, and then the sleeves 800 may be removed from the clamp, leaving the bone pins already in place in the clamp. Therefore, the surgeon needs only to tighten the clamps a single time, to secure the pins in the pin clamp. The sleeve will be described with reference to the pin clamp 504.

FIG. 19-24 shows a hollow protective sleeve 800 and the bone pin 14. The protective sleeve 800 is sized to receive the bone pin 14, and includes a proximal end 802, a distal end 804, and a protective sleeve body 806 extending therebetween. The proximal end 802 includes a cap 808 configured for gripping by a surgeon. The distal end 804 includes a distal tip 810 configured to grip the bone.

Figure 21:
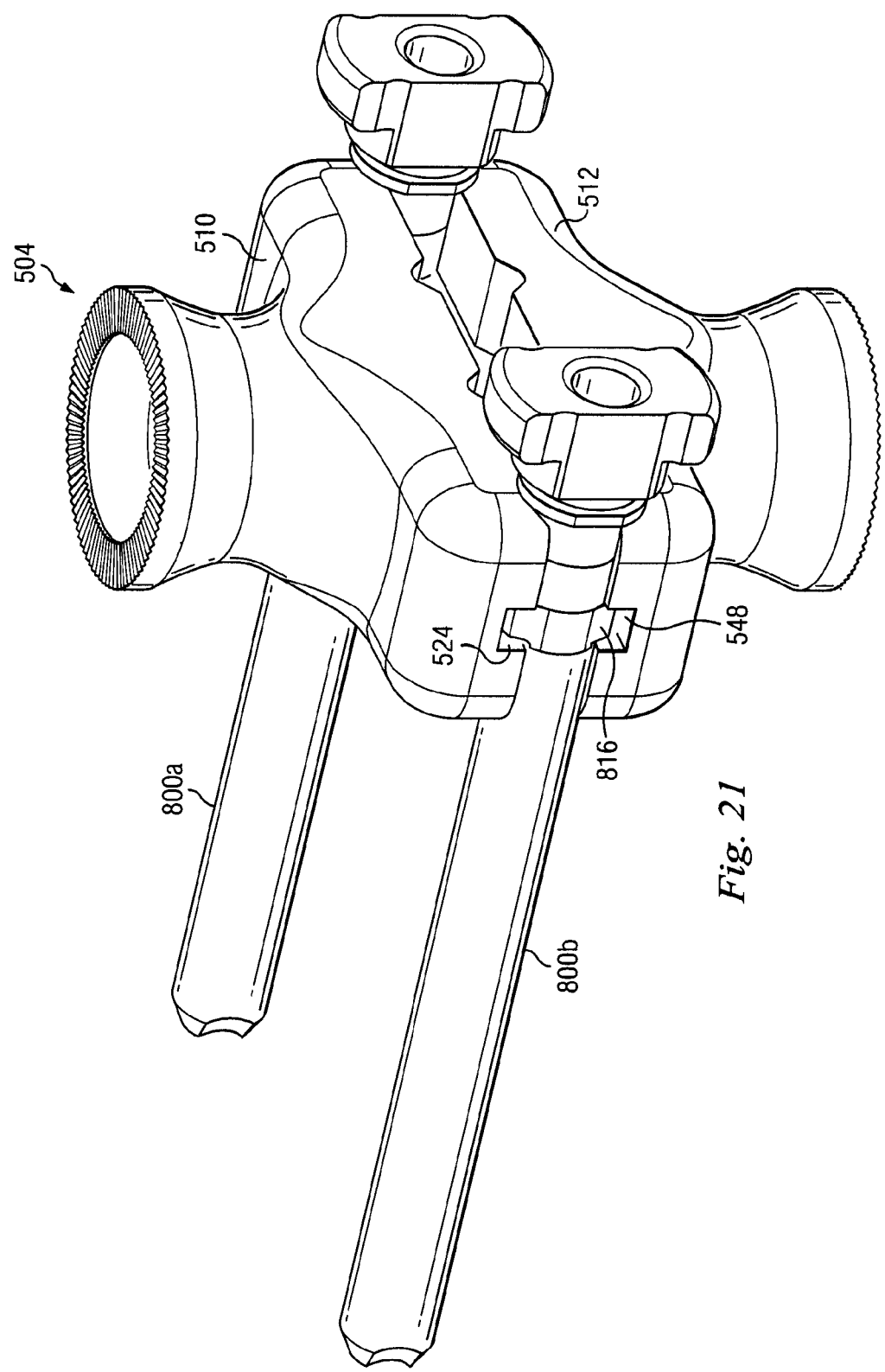
FIG. 21 is an illustration of an exemplary pin clamp with the protective sleeve of FIG. 19 in accordance with one exemplary aspect of the present disclosure.
Figure 22:
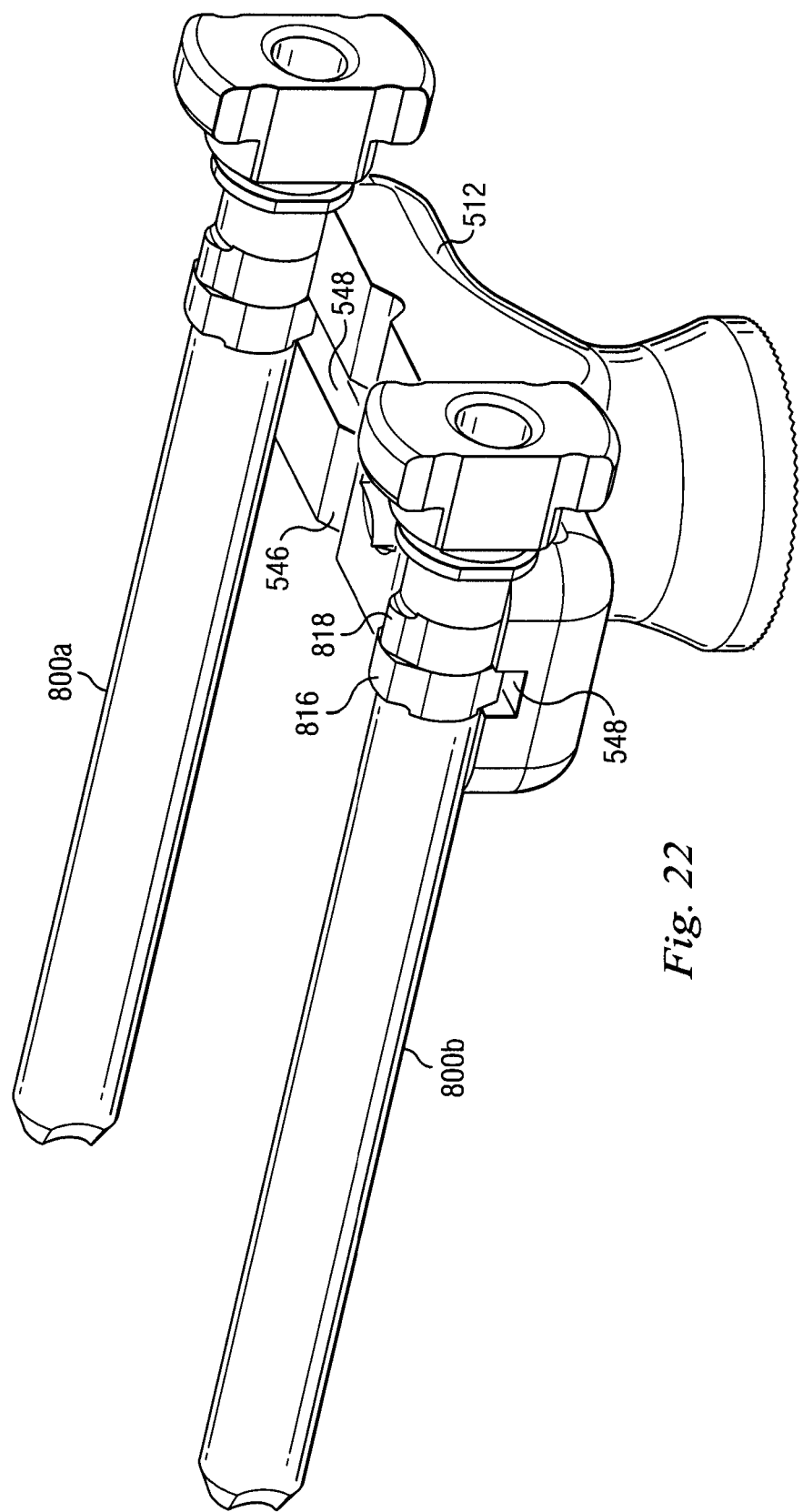
FIG. 22 is an illustration of an exemplary pin jaw with the protective sleeve as in FIG. 21, with the top jaw of the pin clamp removed.
Figure 23:
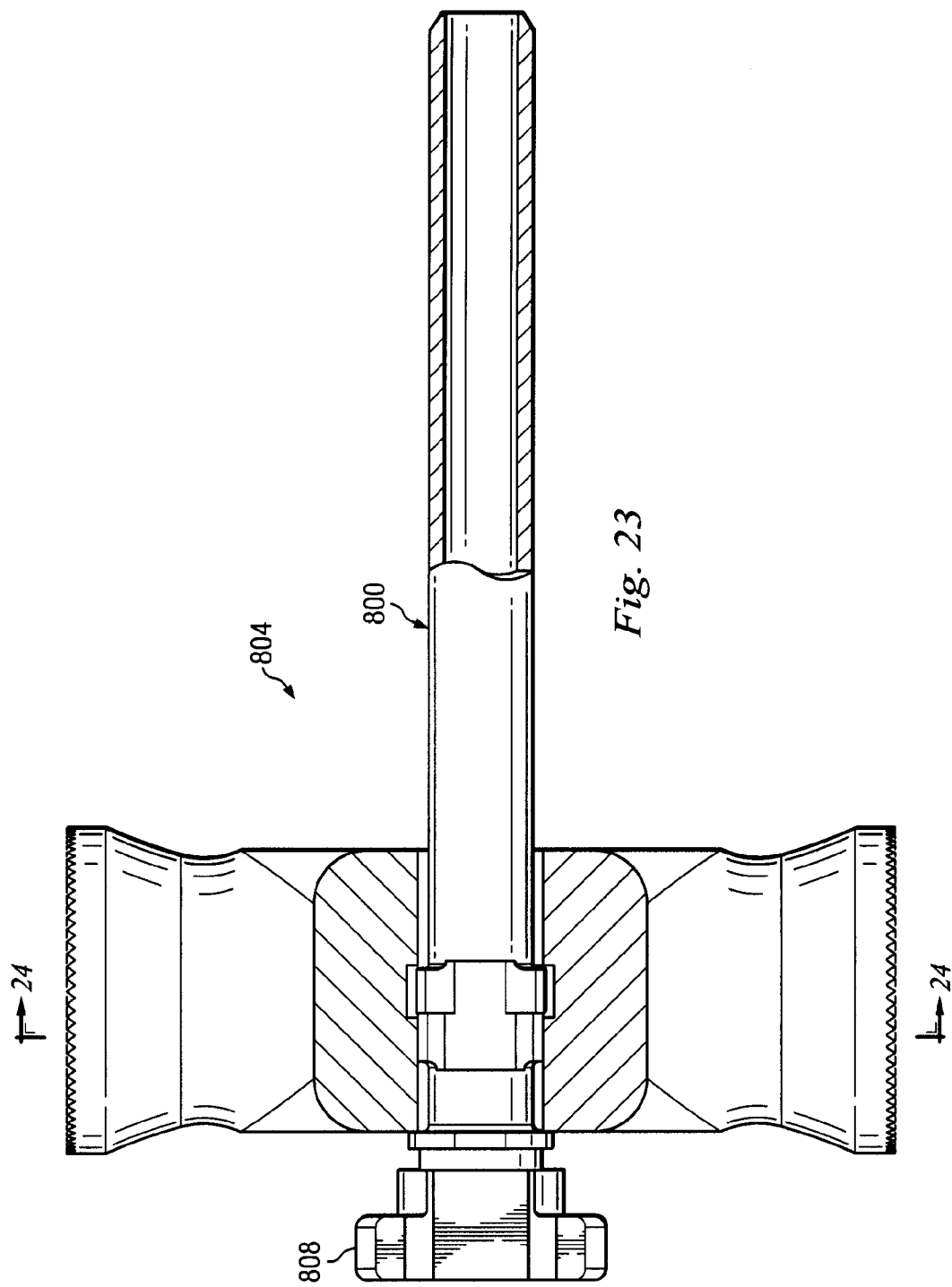
FIG. 23 is an illustration of a side view of an exemplary pin clamp with the protective sleeve of FIG. 19 in accordance with one exemplary aspect of the present disclosure.

The sleeve body 806 is, for purposes of description, divided into a main portion 812 and a clamp interfacing portion 814. The main portion 812 is configured to extend from a pin clamp, such as the clamp 504, and extend to the bone. It has a smooth outer surface that separates and protects soft tissue from the sharp edges and sharp threads on the bone pin 14 as the bone pin 14 is introduced through the sleeve 800 and into the patient and driven into the bone. The clamp interfacing portion 814 includes a partial flange 816 sized to be received into the notches 524, 548 of the pin clamp 504 and includes a projection 818 sized smaller than the partial flange 816 and sized to be received within the grooves 522, 546 formed in the inner clamp faces 538, 514 of the first and second clamp jaws 510, 512. FIG. 21 shows a cross-section taken through the projection 818 and the size differential between the partial flange 816 and the projection 818. FIG. 22 shows two sleeves 800 within the pin clamp 504, and FIG. 23 shows the two sleeves within the pin clamp 504 with the top jaw 510 removed. The partial flange 816 is sized and configured to fit within the notch 548 and prevent the sleeve 800 from sliding axially along the grooves 522, 546 in the jaws 510, 512, when force is applied to the sleeve.

The protective sleeve 800 can be rotated in the grooves 522, 546 between a locked and unlocked position. The locked position corresponds to a position where the partial flange 816 is inserted in the notches 524, 548, and is shown in FIG. 22. That is, when the partial flange 816 is inserted into the notches 524, 548, axial movement of the sleeves is prevented. The unlocked position corresponds to a position where the sleeve 800 is rotated so that the partial flange 816 is rotated out of the notches 524, 548, which is rotated 90 degrees from the position shown in FIG. 22. In this position, the protective sleeve 800 can be axially slid along the grooves 522, 546 and out of the clamp 504 and removed.

In one embodiment, the projection 818 helps locate the sleeve 800 in rotation so that the surgeon can feel and recognize when the tab or partial flange is in the locked position and therefore properly engaged in the notches 524, 548. In this example, the projection 818 may be sized to fit within the grooves 522, 546 when the projection is so aligned. The projection 818 may also be sized to cause the two jaws 510, 512 to move apart against the force of the biasing element(s) (post spring 564) when the protective sleeve 800 is partway between the locked and unlocked position. This can be seen best in FIGS. 23 and 24. In one example, the projection has a profile matching that of the grooves 522, 546.

FIG. 23 is a right side view of the same elements. The flange 816 is shown disposed between facing surfaces forming the walls of the notches 524, 548. These walls restrict the axial motion of the sleeve 800. The cap 808 on the sleeve 800 is configured to make it easy to rotate the sleeve by hand. A section line, 24-24, is shown in this view. As can be seen, the section line is offset from the midline of the clamp 804.

Figure 24:
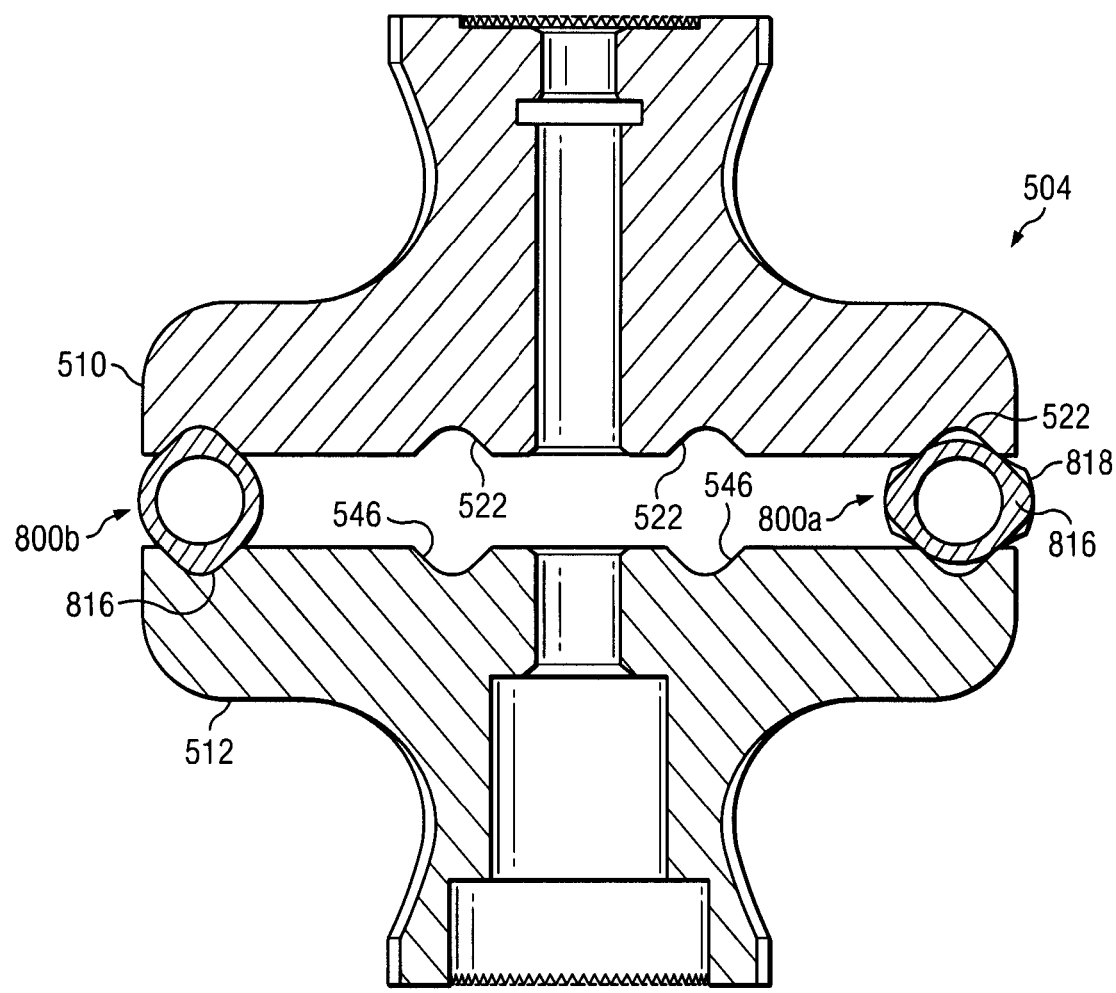
FIG. 24 is an illustration of a cross-sectional view taken along lines 24-24 of FIG. 23 of an exemplary pin clamp with the protective sleeve of FIG. 19 in accordance with one exemplary aspect of the present disclosure.

FIG. 24 is the view of section 24-24. Each of the first and second jaws 510, 512 includes four grooves 522, 546 to hold pins, which have long axes oriented parallel to the desired long axis of the pins. The jaws are biased together because of the post assembly 508 described above. The post spring 564 imposes friction on the protective sleeves 800. The frictional force is dependent on the amount of biasing force, the materials of the clamp and sleeve and the geometry of the slots.

In FIG. 24, the right protective sleeve 800*a* is rotated to a position that allows it to slide along the long axis of the grooves 522, 546, with the partial flange 816 visible between the two clamp jaws. The left protective sleeve 800*b* is rotated to a position where the partial flange 816 is captured in the notches 524, 548 in each clamp jaw 510, 512 (obscured by the clamp jaw) with the projection 818 in the grooves 522, 546, preventing significant motion along the long axis of the grooves 522, 546. Both protective sleeves 800 show the projection 818 that contacts the clamps when the protective sleeve 800 is rotated between the locked and unlocked position.

In use, referring to FIGS. 23 and 24, the protective sleeves 800 are introduced from either a lateral side of the clamp 504 or introduced via axial displacement through the clamp 504 along the pin grooves 522, 546 in the jaws 510, 512. As can be seen in FIGS. 23 and 24, each of the sleeves 800 includes the partial flange 816 and the projection 818. These each have a major axis, shown in the right sleeve 800*a* as extending side-to-side relative to the clamp in FIG. 24, and a minor axis, shown in the right sleeve 800*a* as extending in a vertical direction relative to the clamp in FIG. 24. Although the major and minor axes of the flange 816 and the projection 818 are substantially aligned in this embodiment, the partial flange 816 and the projection 818 have different profiles. The projection 818 may be sized and shaped to have a profile matching that of the grooves 522, 546, but the partial flange 816 is shaped and sized to be larger than the grooves 522, 546, in a manner not matching or receivable into the grooves 522, 546. In order to secure the protective sleeve 800 into the clamp 504, the sleeve 800 may be rotated about its axis so that the partial flange 816 rotates into and lays within the notches 524, 548. When the partial flange 816 is disposed within the notches 524, 548, any axial displacement or translation of the sleeve 800 relative to the clamp 504 in the direction of the sleeve axis is restricted by mechanical interference between the partial flange 816 and the jaw bodies.

Further, as the sleeve 800 is rotated about its axis, the projection 818 moves to be disposed in the manner shown on the left in FIG. 24, with its minor axis extending side-to-side relative to the clamp in FIG. 24, and its major axis extending in a vertical direction, and aligned with the pin slots. Because of the shape of the projection 818 and its relationship with the pin grooves 522, 546, the surgeon can feel when the partial flange 816 is properly engaged in the notches 524, 548. In this example, during rotation, the projection 818 causes the two jaws 510, 512 to be pressed apart against the force of the post spring 564 when the protective sleeve 800 is partway between the locked and unlocked rotated position. When the protective sleeve 800 is aligned so that the partial flange 816 is disposed in the notches 524, 548, the surgeon may feel the projection 818 align with the pin grooves 522, 546.

The sleeves disclosed herein find particular utility with multi-pin clamps where the pins must be aligned properly in order to fit within the clamp. However, it is contemplated that in other embodiments, the sleeves are used with single pin clamps.

Also, it is worth noting that the sleeve 800 may be employed in any clamp, including those with clamping elements in the form of a plurality of bolts and biasing elements in the form of multiple springs. For example, in one aspect, the clamp is made of two jaws that can be pressed together by a plurality of clamping bolts that hold the clamp onto the two or more pins. One or more biasing elements or springs may press the jaws together. On at least one of the two jaws, a recess may be placed in a position along the slot.

In some embodiments, instead of using the notches 524, 548, the front and back faces of the clamp jaws could be used to provide the mechanical interference, with the protector sleeve 800 having a full or partial flange that interfaces with one or both of the front and back faces of the jaws in order to prevent the protector sleeve 800 from sliding against the applied force. In one embodiment the sleeve includes a partial flange as described above on a distal side of the clamp and includes a full flange on the proximal side of the clamp. In other embodiments, only a single flange is used.

In some embodiments, instead of using a biasing element that applies loading onto the sleeves, the use of a flange or partial flange is combined with existing clamps, allowing for the clamp to be tightened finger-tight instead of requiring a tightening load applied with a tool.

In some embodiments, instead of using a notch with a flange to provide mechanical interference, the protective sleeve has a helical feature similar to threads and the clamp has helical recess similar to internal threads and the parts are locked by threading the two parts together.

In use, a surgeon may introduce the sleeve 800 between the jaws of the pin clamp 504 either laterally or axially between the jaws. To insert the sleeve axially, the surgeon may introduce the distal tip into the gaps between the pin clamp jaws formed by the pin-receiving recesses. The tapered tip of the sleeve may distract or separate the jaws against the spring element biasing the jaws closed. The surgeon may axially rotate the sleeve to align the flange to the lateral sides of the jaw clamp so that the flanges can fit into the gap between the jaws. When the flange is between the jaws, the surgeon may align the flange with the lateral notch. He may then engage the sleeve and the jaws by rotating the sleeve about its axis so that the flanges move into the notch or notches in the jaws. As the flange moves into the notches, it is also being moved to a location that creates mechanical interference between the jaw structure and the flange. Accordingly, further axial movement is prevented. As the surgeon rotates the sleeve to introduce the flange into the notch, at the same time, the protrusion rotates from a lateral position to a more vertical position. Because the protrusion projects outwardly from the body, the surgeon can feel the resistance to rotation, as the projection causes the jaws to separate slightly against the force of the spring. As the protrusion continues to rotate, it eventually enters and aligns with the pin-receiving recess, permitting the jaws to resettle toward each other under the force of the spring. Accordingly the surgeon can feel when the protrusion is aligned with the pin-receiving recess as energy is released from the springs. This is also a tactile signal to the surgeon that the flange is properly located in the locking position. With the sleeve secured, the surgeon may introduce the bone-engaging pin, screw or other fixation element into the sleeve. It may then be driven into the bone. Once it is driven into the bone, the surgeon may remove the sleeve by rotating it about its axis until the protrusion leaves the pin-receiving recess, signaling that the flange is out of the notch. The surgeon can then withdraw the sleeve from the pin clamp, leaving the implanted pin in place in the clamp. The clamp can then be tightened as described above.

As discussed above, the clamp of the present disclosure includes components that interdigitate to secure the components relative to each other. For example, referring to the clamping device 100, the inner jaws 116 have elements that interdigitate with the saddles 260 and the saddles interdigitate with the pin jaws 510, 512. In order to reduce the fracture, it is desirable to keep the clamps tight enough to provisionally secure the bone pins or fixation rods, while maintaining the interdigitating components spaced far enough apart to permit suitable reduction, until the external fixation frame is ready for final locking. However, in conventional systems, when clamping devices are tightened sufficiently to frictionally secure the bone pins or fixation rods, the springs between the interdigitating features also compress at least enough that relative rotation results in jumping or partial interference of the interdigitating features. The biasing elements disclosed herein are provided to snug the clamp but the interdigitations will remain apart until the clamps are finally tightened.

As used herein, the term "high spring rate" is intended to include spring rate values sufficient to maintain interdigitating surfaces in a spaced apart relationship while being subjected to loading high enough to create sufficient friction between components to offset the forces of gravity. In other words, the high spring rate maintains the spacing of interdigitating surfaces even when loading has eliminated free movement of components relative to each other in any of rotation, pivoting, or translation. This is typically a spring rate of about 30 lbs/inch or greater.

As used herein, the term "low spring rate" is intended to include spring rate values less than 30 lbs/inch.

The terms "higher spring rate" and "lower spring rates" are given their ordinary meaning of relative terms, and are not bound or limited by the definitions of "high spring rate" and "low spring rate."

The spring elements are described with reference to FIGS. 25A-25C. These figures show the clamp 500 in different degrees of tightening. Referring to these figures, the clamps 500 include biasing elements corresponding to coil springs 114 and 564. These have a low spring rate and high travel and cooperate with the spherical washer 110a or the fixation post 560 to control the biasing force on the jaws when in the open and closed position, when the locking nuts 112 are in their loosest state. The spring washers 268 have a low travel but higher spring rate and are disposed between the interdigitating saddle 260 and spacer components 264 and between the interdigitating saddles 260 and the pin clamp 504. These spring washers 268 keep the interdigitating features from contacting until after a sufficiently high load has been applied by the locking nuts 112. Here, the spring rate of the spring washers 268 is selected to be sufficient to fine tune the amount of friction force between the saddles and jaws or between the saddles and pin jaws, allowing a large contact force to be generated prior to the interdigitating surfaces closing. In some examples, the spring washers 268 have a spring rate of about 50 lbs/inch or greater.

Figure 25A:
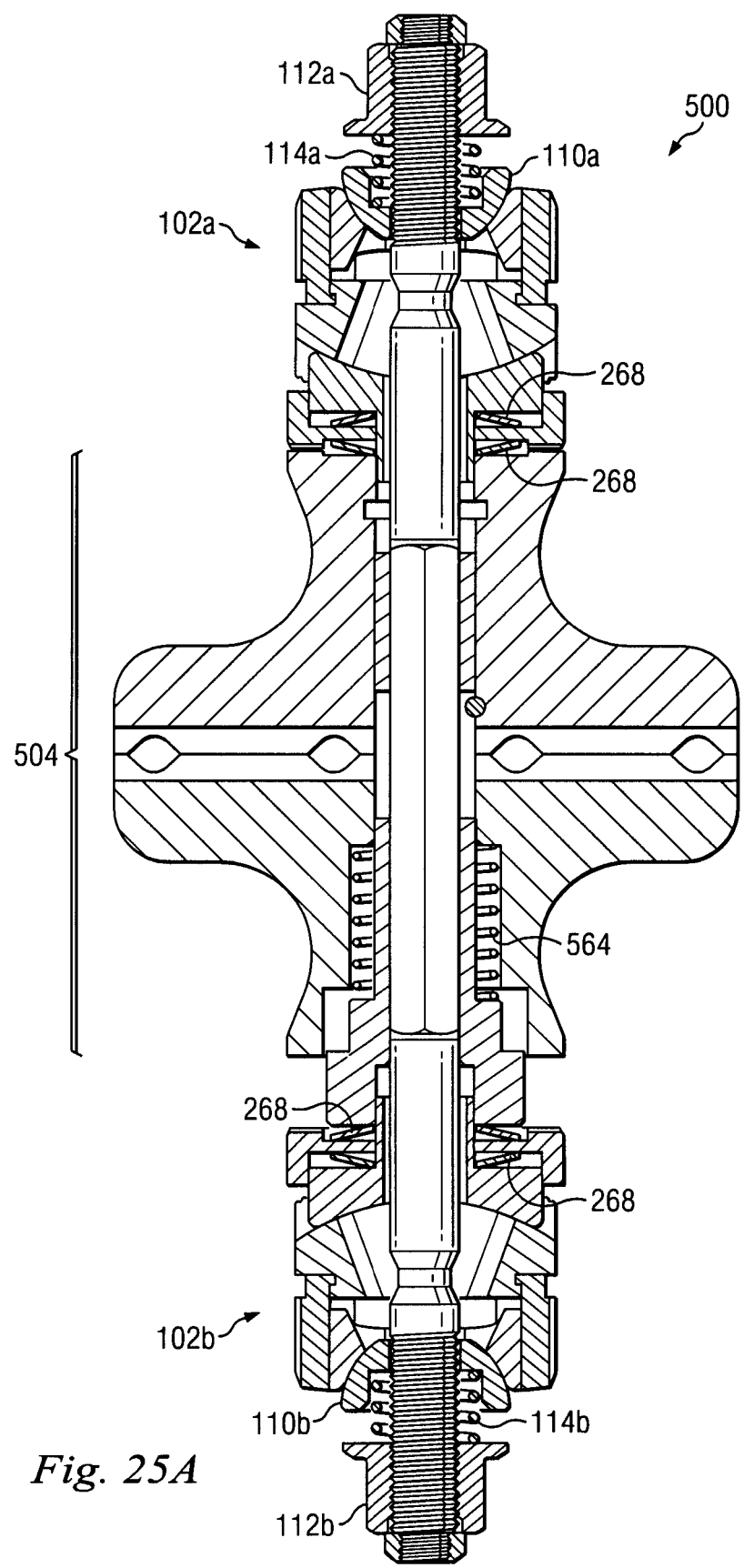
FIGS. 25A-25C are illustrations of a cross-sectional view of the clamping device of FIG. 13 in different degrees of tightening in accordance with one exemplary aspect of the present disclosure.
Figure 25B:
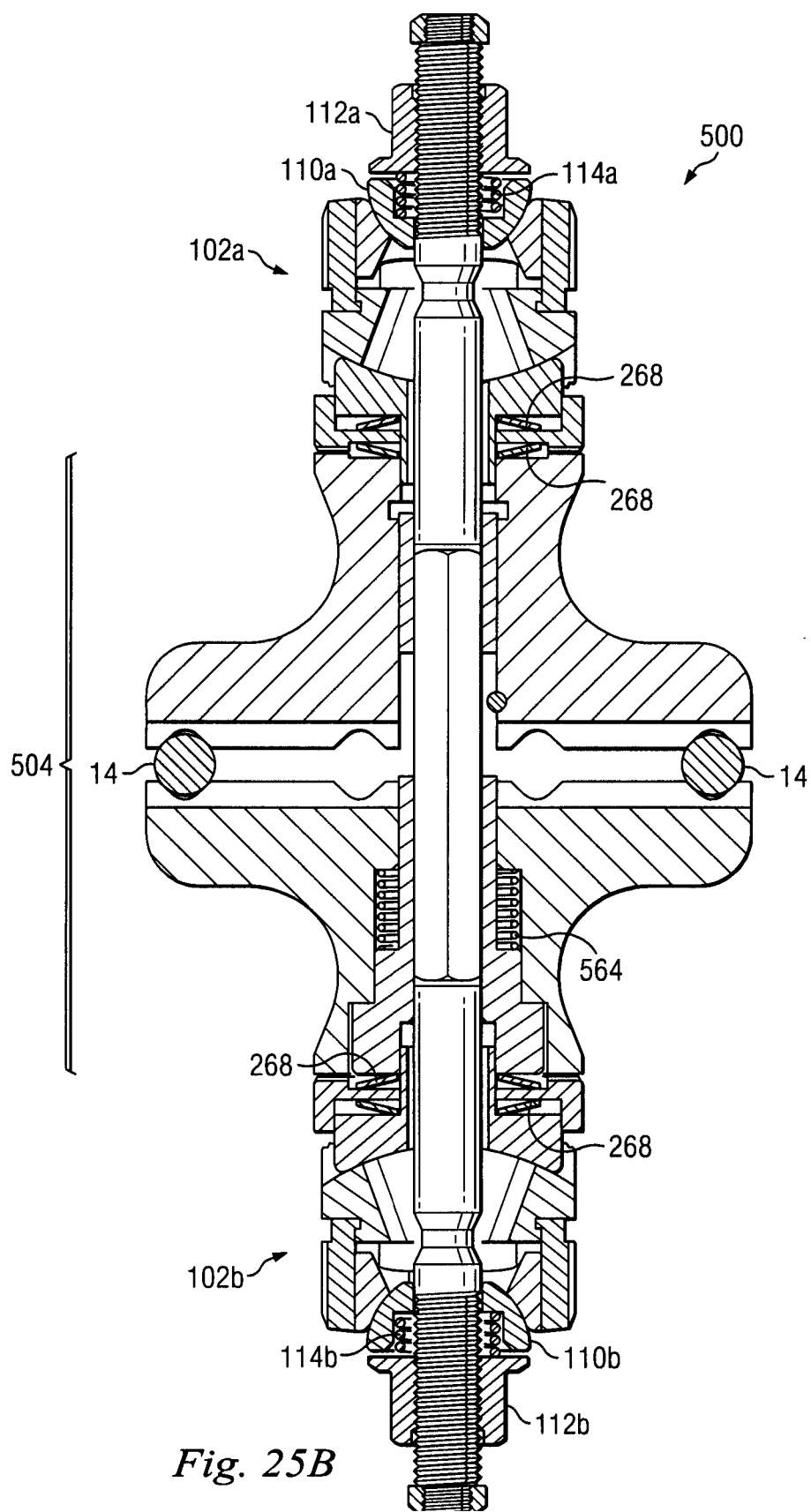
Figure 25C:
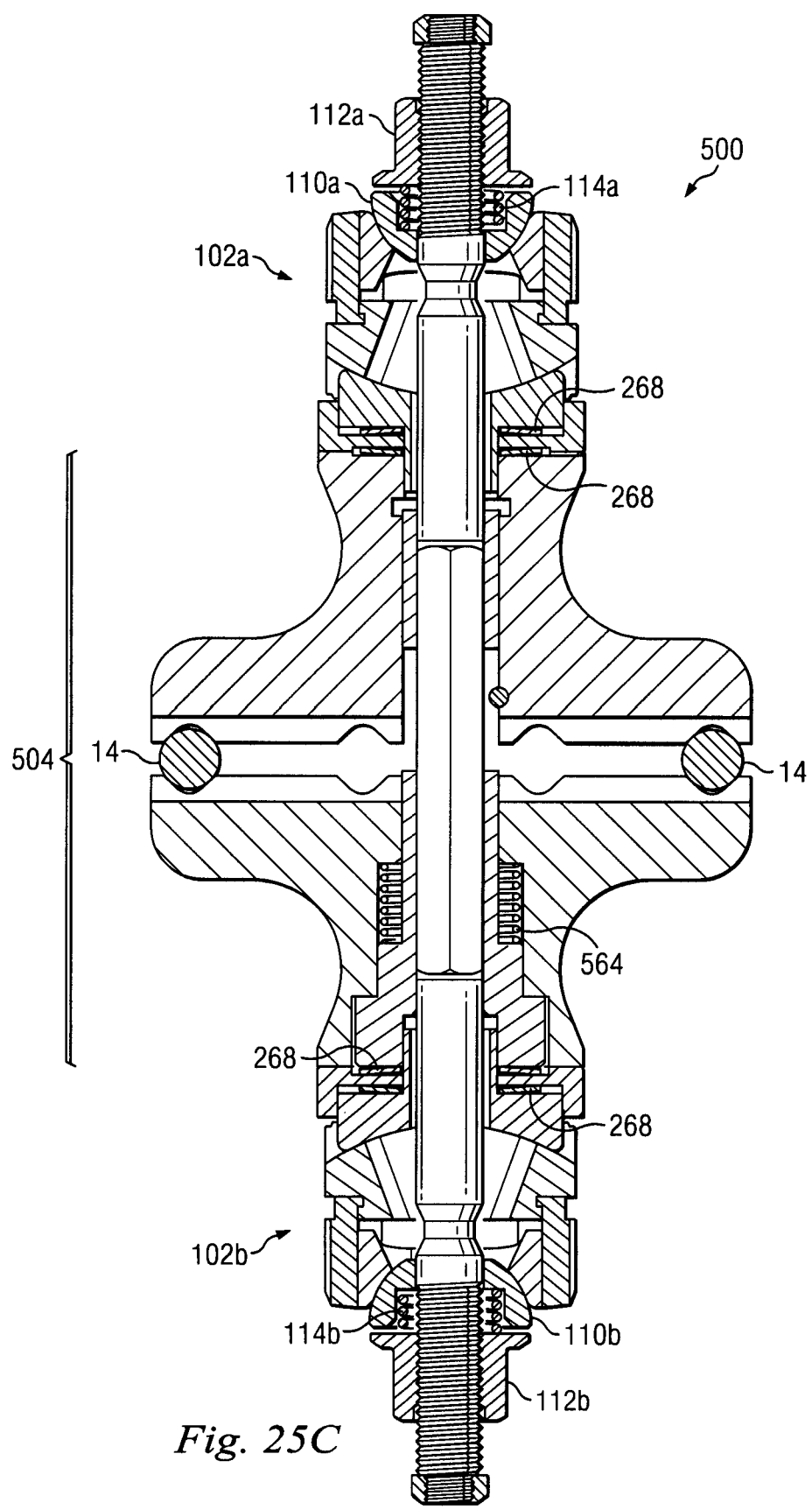

FIG. 25A shows the clamp 500 in an empty state, with the low spring rate coil springs 114, 268 relaxed and with the spring washers 268 relaxed. FIG. 25B shows the clamp 500 after insertion of fixation elements. In this case, bone pins have been inserted into the pin clamp 504. Other embodiments include the tissue protector discussed above. After insertion of fixation elements, whether pins, rods, tissue protector, or other element, into the clamping device, the low spring rate coil springs 114, 268 become partially compressed. Depending on the arrangement, compression of the low spring rate springs may occur even before the locking nut 112 is advanced on the stud 562.

Because the coil springs have a low spring rate, the coil springs compress. Because the spring washers 268 have a high spring rate, they do not yet compress. With the coil springs partially compressed, the surgeon may apply additional friction onto the bone pins by tightening one of the locking nuts 112. As the locking nut 112 advances, the coils springs continue to compress until they are fully compressed, becoming, for force purposes, a rigid body. Even still, the high spring rate spring washers 268 do not yet compress. This enables the surgeon to adjust the level of friction on the bone pins and elements without the interdigitation surfaces engaging. That is, tailoring of the frictional forces is accomplished by further compression of the coil springs 114, 268 prior to a deflection of the washer spring 268 such that the interdigitating features engage each other. With the clamp in this state, the surgeon can still manipulate the fixation system with the pins or rods in a provisionally secured state.

The low biasing spring elements, such as the coil springs 114, 268, are intended to bias the components together to give the user tactile feel when inserting components and to give a slight initial grip of the fixation elements. For example the user can feel when the tissue protector is rotated to the correct position, as explained above, because the low spring rate biasing element causes the pin jaws to be pushed together, giving the user a tactile feel for when the major or minor diameter is aligned with the pin slot. This sense of feel requires some measurable travel and a relatively low level of force, as the tissue protector is twisted with fingertips.

The friction applied to the fixation elements by the low spring rate biasing elements may be sufficient to withstand the force of gravity, but beyond that, they allow sliding of the components along the element. When reducing the fracture, the surgeon may prefer to have the clamp roll, pitch and yaw rotations move smoothly, but with a higher friction than can be applied with a low spring rate biasing element. By turning the locking nut 112 further, the amount of force applied to the clamp interconnections and the fixation elements can be increased to higher levels. With high spring rate biasing elements interposed between the interdigitations, the smooth surfaces remain in contact and the clamp subassemblies can be smoothly rotated about the different axes without the jumping that would occur if the interdigitations were in contact.

When the surgeon has arranged the clamping device 500 as desired on the external fixation components, such as, for example, bars, rods, or bone pins, the clamping device 500 can be locked by further turning one of the locking nuts 112 until the high spring force of the spring washers 268 is overcome, and the opposed interdigitating splines engage each other. This condition is shown in FIG. 25C, where the coil springs and the spring washers 268 are compressed, thereby fully engaging the interdigitating surfaces. In some examples, for this to happen, the springs 114, 564 may be entirely compressed, such that it forms a solid cylinder. In this condition, any further advancement of the locking nut 112 will begin to compress the high bias rate spring washers 268. This compression continues until the interdigitating splines are fully engaged and the facing components are locked against rotation by mechanical interference.

In this example, the high spring rate spring washers 268 are high force-low travel springs. Accordingly, their compression does little to change the overall positioning of the clamps relative to each other. The low spring rate coil springs 114 are low force-high travel springs. In some embodiments, the low spring rate springs 114 is intended to have a travel length more than double that of the high spring rate spring washers 268.

Depending on the arrangement of the jaws and the biasing elements, the low spring rate springs 114, 564 may bias the jaws in an open position for receiving a first external fixation element. In other embodiments, the low spring rate springs 114 may bias the jaws in a closed position.

The particular clamping devices disclosed herein exemplify two different situations where the high spring rate biasing element 268 could be employed. It is obvious that a simpler clamp construct with only one interdigitating surface could still employ the invention to improve the feel when adjusting that clamping device. Therefore, the high spring rate biasing element 268 could be placed between two one-piece jaws or between any two jaw sets. It could also be placed between a jaw set and another frame component such as a monotube external fixation frame.

Figure 26:
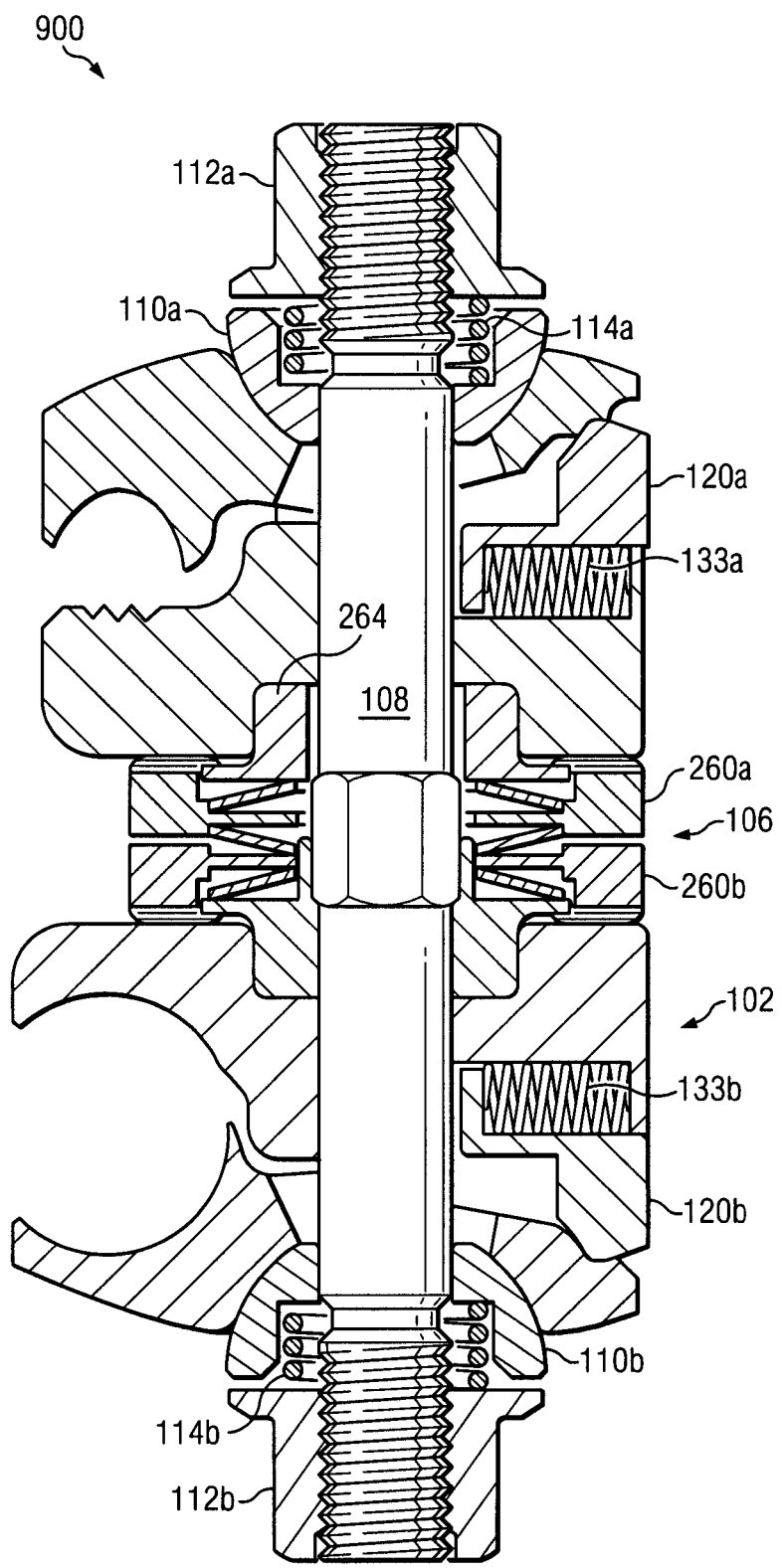
FIG. 26 is an illustration of an alternative clamping device having higher and lower spring rate biasing elements.

FIG. 26 illustrates an alternative clamping device 900 having higher and lower spring rate biasing elements. Many of the features of the clamping device 900 are similar to the features discussed above, and those reference numerals are provided here. The clamping device 900 is a two-clamp system and includes a pin clamp and a rod clamp. Both the pin clamp and the rod clamp include inner and outer jaws. The inner jaws having interdigitating features as described above. A saddle assembly separates the first and second jaws. The saddle assembly includes spacers and saddle component as described above. Additional details about the clamping device may be found in incorporated U.S. patent application Ser. No. 13/175,343 filed Jul. 1, 2011. The clamping device 900 shown here includes the high spring rate biasing elements 268 and the low spring rate biasing elements 114. Accordingly, the low spring rate biasing elements 114 compress before the high spring rate biasing elements in the manner described above.

In some embodiments, the Belleville spring washer 268 is replaced by another high force biasing element such as a wavy spring washer or a leaf spring. In some embodiments, the jaw sets could be replaced with jaws that grasp other external fixation components or jaws that grab more than one external fixation component. In some embodiments, it is possible to use jaws that are self-biasing or do not require biasing elements with the high spring rate biasing element 268 maintaining separation of the interdigitating features until a high force is applied.

Some embodiments provide smooth operation and manipulation of components. However, in another exemplary embodiment, a biasing element is selected to have a spring rate that allows for some mechanical overlap of interdigitating features in a manner permitting clicking during movement of the clamping device relative to the external fixation component. For example, some embodiments include a biasing element with a spring rate selected to allow for some mechanical overlap of interdigitating features in a manner permitting clicking during movement of the clamping device relative to the external fixation component. Some of these embodiments include a near balance of the spring rate of the spring 114 and the spring washer 268, such that the interdigitating features only partially engage, such that movement results in an audible or tactile clicking. In such embodiments, the interdigitating features act as detents.

In some embodiments, the high spring rate spring washer 268 allows the surgeon to fine tune the friction so that the interdigitating components are spaced apart and will move smoothly relatively to each other. A loose component would fall into undesired positions, and interdigitated components can jump when being articulated. Low spring rate helical wire springs may be of insufficient spring rate to space the interdigitating components apart while still having sufficient friction to hold components for smooth movement and placement.

It should be noted that some embodiments do not require that the coil spring be bottomed out. For example, some embodiments have rigid structural stops that engage and limit the compression range of the springs.

The foregoing has outlined features of several embodiments. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

We claim:

1. A clamping device for an external fixation system, comprising:
   a post component having a yaw axis;
   a first clamp secured adjacent to a first end of the post component and rotatable about the yaw axis, the first clamp comprising a pair of jaws cooperatively arranged to capture a fixation element, the jaws being movable between an open position that permits the fixation element to be placed between the jaws and a closed position that restricts removal of the fixation element from between the jaws;
   a second clamp secured adjacent to a second end of the post component and rotatable about the yaw axis relative to the first clamp;
   a tightening assembly associated with the first clamp, wherein the tightening assembly comprises:
      a spherical washer received in a depression in an outer surface of the first clamp;
      a tightening component threadably engaging the first end of the post component adjacent the first clamp;
      a first biasing element disposed between the spherical washer and the tightening component,
      wherein an action of tightening the tightening component simultaneously locks both the first and second clamps and locks their rotation about the yaw axis; and
   a latch engaged with and moveable relative to both of the jaws, the latch being configured to translate linearly relative to the jaws to cause the jaws to be arranged in the open position and the closed position.

2. The clamping device of claim 1, further comprising an intervening member secured to the post component and disposed between and separating the first clamp and the second clamp, and wherein the pair of jaws of the first clamp comprises:
   a first inner jaw adjacent the intervening member; and
   a first outer jaw,
   wherein the spherical washer and the depression facilitate articulation of the first outer jaw relative to the post component.

3. The clamping device of claim 1, wherein the second end of the post component adjacent the second clamp comprises a spherical head received in a second depression in an outer surface of the second clamp.

4. The clamping device of claim 3, further comprising an intervening member secured to the post component and disposed between and separating the first clamp and the second clamp, and wherein the second clamp comprises:
   a second inner jaw adjacent the intervening member; and
   a second outer jaw,
   wherein the spherical head and the second depression facilitate articulation of the second outer jaw relative to the post component.

5. The clamping device of claim 1, wherein the tightening component comprises a first tightening component, and further comprising a second tightening component associated with the second clamp, wherein each of the first and second tightening components are configured in a manner that an action of tightening one of the tightening components simultaneously locks both the first and second clamps.

6. The clamping device of claim 5, wherein the tightening assembly comprises a first tightening assembly and the tightening component comprises a first tightening component, and further comprising a second tightening assembly associated with the second clamp, wherein the second tightening assembly comprises:
   a second spherical washer received in a second depression in an outer surface of the second clamp;
   the second tightening component threadably engaging the second end of the post component adjacent the second clamp; and
   a second biasing element disposed between the second spherical washer and the second tightening component.

7. The clamping device of claim 6, further comprising an intervening member secured to the post component and disposed between and separating the first clamp and the second clamp, and wherein the first and second biasing elements comprise first and second low spring rate biasing elements, and further comprising:

a plurality of high spring rate biasing elements,
wherein at least one of the high spring rate biasing elements is disposed between the first clamp and the intervening member and at least one of the high spring rate biasing elements is disposed between the second clamp and the intervening member,
wherein each of the first and second low spring rate biasing elements comprises a spring rate less than 30 pounds per inch, and
wherein each of the high spring rate biasing elements comprises a spring rate of at least 50 pounds per inch.

8. The clamping device of claim 7, wherein each of the first and second low spring rate biasing elements comprises a helical spring and wherein each of the high spring rate biasing elements comprises a spring washer.

9. The clamping device of claim 6, further comprising an intervening member secured to the post component and disposed between and separating the first clamp and the second clamp, and wherein the second clamp comprises:
a second inner jaw adjacent the intervening member; and
a second outer jaw,
wherein the spherical washer and the second depression facilitate articulation of the second outer jaw relative to the post component.

10. The clamping device of claim 1, comprising a first base component having a cylindrical surface having a pitch axis, wherein the pair of jaws of the first clamp comprises:
a first outer jaw;
a first inner jaw having an inner surface facing the outer jaw, the outer and inner jaws together forming an opening for receiving a first fixation element of the external fixation system, the first inner jaw and first outer jaw having a roll axis alignable with a longitudinal axis of the fixation element, the clamp and post component being rotatable about the roll axis, the first inner jaw also having a cylindrical outer-facing surface, the cylindrical surface of the first base component interfacing with the cylindrical outer facing component on the inner jaw, the first outer and inner jaws being rotatable relative to the base component and the post component about the pitch axis.

11. The clamping device of claim 10, wherein the cylindrical surface of the first base component is a concave surface and the cylindrical surface of the first inner jaw is a convex surface.

12. The clamping device of claim 10, wherein the first base component and the first inner jaw each have friction enhancing features, the friction enhancing features selectively interdigitating with each other to restrict rotation about the pitch axis.

13. The clamping device of claim 12, wherein the friction enhancing features are splines.

14. The clamping device of claim 1, wherein the post component and the second clamp are structurally arranged to prevent relative rotation about the yaw axis.

15. The clamping device of claim 1, wherein the first and the second clamps each comprise friction enhancing features, the friction enhancing features preventing relative rotation about the yaw axis when the tightening component is tightened.

16. The clamping device of claim 1, wherein the first biasing element comprises a helical spring disposed about the post component between the spherical washer and the tightening component.

17. A clamping device for an external fixation system, comprising:
a post component having a yaw axis;
a first clamp secured adjacent to a first end of the post component and rotatable about the yaw axis, the first clamp comprising a pair of jaws cooperatively arranged to capture a fixation element, the jaws being movable between an open position that permits the fixation element to be placed between the jaws and a closed position that restricts removal of the fixation element from between the jaws;
a second clamp secured adjacent to a second end of the post component and rotatable about the yaw axis relative to the first clamp;
a high spring rate biasing element interposed between the first and second clamps; and
a tightening assembly associated with the first clamp, wherein the tightening assembly comprises:
a tightening component engaging the first end of the post component adjacent the first clamp;
a low spring rate biasing element disposed between the tightening component and the first clamp,
wherein an action of tightening the tightening component simultaneously locks both the first and second clamps and locks their rotation about the yaw axis; and
a latch engaged with and moveable relative to both of the jaws, the latch being configured to translate linearly relative to the jaws to cause the jaws to be arranged in the open position and the closed position.

18. The clamping device of claim 17, wherein the tightening component comprises a first tightening component, and further comprising a second tightening component associated with the second clamp, wherein each of the first and second tightening components are configured in a manner that an action of tightening one of the tightening components simultaneously locks both the first and second clamps.

19. The clamping device of claim 18, wherein the tightening assembly comprises a first tightening assembly and the low spring rate biasing element comprising a first low spring rate biasing element, and further comprising a second tightening assembly associated with the second clamp, wherein the second tightening assembly comprises:
the second tightening component engaging the second end of the post component adjacent the second clamp; and
a second low spring rate biasing element disposed between the second tightening component and the second clamp.

20. The clamping device of claim 19, wherein each of the first and second low spring rate biasing elements comprises a spring rate less than 30 pounds per inch, and wherein each of the first and second high spring rate biasing elements comprises a spring rate of at least 30 pounds per inch.

21. The clamping device of claim 20, wherein each of the first and second high spring rate biasing elements comprises a spring rate of at least 50 pounds per inch.

22. The clamping device of claim 19, wherein each of the first and second low spring rate biasing elements comprises a helical spring and wherein the high spring rate biasing element comprises a spring washer.

* * * * *